US008455214B2

(12) United States Patent
Jacobs, Jr. et al.

(10) Patent No.: US 8,455,214 B2
(45) Date of Patent: Jun. 4, 2013

(54) METHODS FOR DETERMINING CHEMOTHERAPEUTIC AGENTS TARGETING ALPHA-GLUCAN PATHWAYS AND USES THEREOF

(75) Inventors: William R. Jacobs, Jr., Pelham, NY (US); Rainer Kalscheuer, Hilden (DE); Stephen Bornemann, Norwich (GB); Karl Syson, Norwich (GB)

(73) Assignees: Albert Einstein College of Medicine of Yeshiva University, Bronx, NY (US); Plant Bioscience Limited, Norwich (GB)

( * ) Notice: Subject to any disclaimer, the term of this patent is extended or adjusted under 35 U.S.C. 154(b) by 118 days.

(21) Appl. No.: 12/925,633

(22) Filed: Oct. 26, 2010

(65) Prior Publication Data

US 2011/0124593 A1 May 26, 2011

Related U.S. Application Data

(60) Provisional application No. 61/280,818, filed on Nov. 9, 2009.

(51) Int. Cl.

| | |
|---|---|
| ***C12Q 1/18*** | (2006.01) |
| ***C12Q 1/48*** | (2006.01) |
| ***C12Q 1/25*** | (2006.01) |
| ***C12N 9/12*** | (2006.01) |
| ***G01N 33/573*** | (2006.01) |
| ***G01N 33/569*** | (2006.01) |
| *C12Q 1/68* | (2006.01) |
| *C12N 9/52* | (2006.01) |

(52) U.S. Cl.
USPC ............. 435/32; 435/6.15; 435/7.71; 435/15; 435/29; 435/194

(58) Field of Classification Search
USPC ............. 435/6.15, 7.71, 15, 29, 32, 194, 220, 435/863, 866
See application file for complete search history.

(56) References Cited

U.S. PATENT DOCUMENTS

2006/0121576 A1 6/2006 Igarashi et al.

OTHER PUBLICATIONS

Karlscheuer et al. Self-poisoning of Mycobacterium tuberculosis by targeting GlgE in an α-glucan pathway. Nature Chemical Biology (May 2010, published online Mar. 21, 2010) vol. 6, pp. 376-384.*
Elbein et al. Last Step in the Conversion of Trehalose to Glycogen A Mycobacterial Enzyme That Transfers Maltose From Maltose 1-Phosphate to Glycogen (Mar. 26, 2010) The Journal of Biological Chemistry, vol. 285, pp. 9803-9812.*
Syson et al. Structure of Streptomyces Maltosyltransferase GlgE, a Homologue of a Genetically Validated Anti-tuberculosis Target (Nov. 4, 2011) The Journal of Biological Chemistry, vol. 286, pp. 38298-38310.*
Meissner et al. 1998. Thermotoma maritima maltosyltransferase, a novel type of maltodextrin glycosyl transferase acting on starch and malto-oligosaccharides. European Journal of Biochemistry, vol. 250, pp. 1050-1058.*
Mukai et al. 2006. Purification, Characterization, and Gene Cloning of a Novel MAltosyltransferase from an Arrthrobacter globiformis Strain that Produces an Alternating α-1, 4- and α-1, 6-Cyclic Tetrasaccharide from Starch. Applied and Environmental Microbiology, vol. 72, pp. 1065-1071.*
Elbein, et al.2010. Last Step in the Conversion of Trehalose to Glycogen a Mycobacterial Enzyme That Transfers Maltose From Maltose 1-Phosphate to Glycogen. Journal of Biological Chemistry, vol. 285, pp. 9803-9812.*
Kalscheuer R et al. Self-poisoning of Mycobacterium tuberculosis by targeting GlgE in an α-glucan pathway, Nature Chemical Biology, May 2010, 6: 376-384. Epubl Mar. 21, 2010.

* cited by examiner

*Primary Examiner* — Jon P Weber
*Assistant Examiner* — Kailash C Srivastava
(74) *Attorney, Agent, or Firm* — Amster Rothenstein & Ebenstein LLP

(57) ABSTRACT

The present invention provides methods for determining a putative antibacterial, the methods comprising determining whether the putative antibacterial inhibits GlgE or Rv3032. The present invention also provides the antibacterial, the pharmaceutical composition and the method of making the antibacterial as well as a method of treating a subject infected with a bacterial comprising administration of the antibacterial.

14 Claims, 12 Drawing Sheets

SEQUENCE LISTING

```
<160> NUMBER OF SEQ ID NOS: 8

<210> SEQ ID NO 1
<211> LENGTH: 35
<212> TYPE: DNA
<213> ORGANISM: Artificial Sequence
<220> FEATURE:
<223> OTHER INFORMATION: primer for glgEMsmeg

<400> SEQUENCE: 1

tttttaagc ttgtgaggag tggttgggtg gccgg                                35


<210> SEQ ID NO 2
<211> LENGTH: 36
<212> TYPE: DNA
<213> ORGANISM: Artificial Sequence
<220> FEATURE:
<223> OTHER INFORMATION: primer for glgEMsmeg

<400> SEQUENCE: 2

ttttttatcg attcattccc tgcgtagcaa gtcgag                              36


<210> SEQ ID NO 3
<211> LENGTH: 36
<212> TYPE: DNA
<213> ORGANISM: Artificial Sequence
<220> FEATURE:
<223> OTHER INFORMATION: primer for glgBMsmeg

<400> SEQUENCE: 3

ttttttaagc ttatgacgag aagcagcaat caactc                              36


<210> SEQ ID NO 4
<211> LENGTH: 37
<212> TYPE: DNA
<213> ORGANISM: Artificial Sequence
<220> FEATURE:
<223> OTHER INFORMATION: primer for glgBMsmeg

<400> SEQUENCE: 4

ttttttatcg atctaagccg gctcgaacca gagcatc                             37


<210> SEQ ID NO 5
<211> LENGTH: 35
<212> TYPE: DNA
<213> ORGANISM: Artificial Sequence
<220> FEATURE:
<223> OTHER INFORMATION: primer for glgEMtb

<400> SEQUENCE: 5

ttttttaagc ttgtgagtgg ccgggcaatc ggaac                               35
```

-continued

<210> SEQ ID NO 6
<211> LENGTH: 34
<212> TYPE: DNA
<213> ORGANISM: Artificial Sequence
<220> FEATURE:
<223> OTHER INFORMATION: primer for glgEMtb

<400> SEQUENCE: 6 tttttgata tctcacctcc tgcgcagcag cgtg 34

<210> SEQ ID NO 7
<211> LENGTH: 38
<212> TYPE: DNA
<213> ORGANISM: Artificial Sequence
<220> FEATURE:
<223> OTHER INFORMATION: primer for treSMtb

<400> SEQUENCE: 7
ttttttcagc tgcaatgaac gaggcagaac acagcgtc 38

<210> SEQ ID NO 8
<211> LENGTH: 34
<212> TYPE: DNA
<213> ORGANISM: Artificial Sequence
<220> FEATURE:
<223> OTHER INFORMATION: primer for treSMtb

<400> SEQUENCE: 8
ttttttaagc ttcataggcg ccgctctccc ccgc 34

METHODS FOR DETERMINING CHEMOTHERAPEUTIC AGENTS TARGETING ALPHA-GLUCAN PATHWAYS AND USES THEREOF

CROSS-REFERENCE TO RELATED APPLICATION

This application claims the benefit of U.S. Provisional Patent Application No. 61/280,818, filed on Nov. 9, 2009, the content of which is herein incorporated by reference.

STATEMENT OF GOVERNMENT SUPPORT

This invention was made with government support under grant numbers AI26170 and AIO-68135 awarded by the National Institutes of Health. The government has certain rights in the invention.

FIELD OF THE INVENTION

The present invention relates to methods for determining antibacterials that inhibit α-glucan pathways, and uses thereof.

BACKGROUND OF THE INVENTION

Throughout this application various publications are referred to in parenthesis. Full citations for these references may be found at the end of the specification. The disclosures of these publications are hereby incorporated by reference in their entirety into the subject application to more fully describe the art to which the subject invention pertains.

*Mycobacterium tuberculosis* (Mtb), the etiological agent of tuberculosis (TB), is the leading cause of mortality due to bacterial pathogens, claiming about two million lives annually. With the advent of the antibiotic era, TB became treatable and at one point eradication was believed possible. However, in recent years TB has reemerged as a major global health threat due to the disastrous combination of poverty, a deadly synergy with HIV, and the emergence of extensively-drug-resistant strains (XDR-TB) that are virtually untreatable with current chemotherapies (1). To counter this resurgence of TB and to combat XDR-TB, new treatment options are urgently needed based on novel classes of bacterial targets very different from those of the antibiotics currently in use.

Identification of essential gene functions required for in vitro growth of Mtb is a pivotal strategy for discovering new drug targets due to the ease of screening for antibacterial compounds and testing for resistance. A genome-wide screen of a saturated Mtb transposon mutant library using microarray-based transposon site hybridization (TraSH) technology indicated that more than 600 genes (~15%) may be required for in vitro growth (2). However, the rational development of specific inhibitors is hampered by ignorance of the functions of many of these essential candidates. Identification of nonessential gene functions that are dispensable for in vitro growth but are required for virulence is an additional valuable source of drug targets, but inhibitor screening for these candidates is typically much more difficult. Using the TraSH technique, 194 of the nonessential Mtb genes were found to be specifically required for in vivo growth in mice (3). Given that Mtb is an obligate intracellular pathogen highly adapted to the human host, with no known significant environmental niche, the large number of genes dispensable for in vitro growth and virulence is surprising. This high degree of gene dispensability probably reflects extensive genetic redundancy or functional homeostatic buffering within essential processes, so that mutations in single genes are often compensated for by other genes. This means that many "synthetic lethal" pathways are certainly present in Mtb. "Synthetic lethality" describes any combination of two separately non-lethal mutations that jointly lead to inviability. In yeast, striking synthetic lethal genetic interactions in genome-wide studies have been demonstrated, revealing that most nonessential genes have several synthetic lethal interactions with other genes (4, 5). Identification of synthetic lethal pathways in Mtb would thus greatly increase the repertoire of drug target candidates.

New chemotherapeutics are urgently required to control the tuberculosis pandemic fueled by the emergence of multi-drug- and extensively-drug-resistant Mtb strains and the bacterium's catastrophic alliance with HIV. The present invention answers this need by providing new assays for the development of chemotherapeutics to combat tuberculosis and other opportunistic pathogens. The present invention provides assays for the development of chemotherapeutics targeting the ubiquitous and conserved GlgE and Rv3032 α-glucan pathways.

SUMMARY OF THE INVENTION

The present invention provides a method for determining a putative antibacterial, the method comprising determining whether the putative antibacterial inhibits GlgE. The present invention also provides a method for determining a putative antibacterial, the method comprising determining whether the putative antibacterial inhibits Rv3032.

The present invention further provides an antibacterial identified by the method for determining a putative antibacterial comprising determining whether the putative antibacterial inhibits GlgE or by the method for determining a putative antibacterial comprising determining whether the putative antibacterial inhibits Rv3032.

The present invention additionally provides a method of treating a subject infected with a bacterium, the method comprising administering to the subject a GlgE inhibitor in an amount effective to treat the bacterial infection. The present invention provides a method of treating a subject infected with a bacterium, the method comprising administering to the subject a GlgE inhibitor and a Rv3032 inhibitor in an amount effective to treat the bacterial infection.

The present invention provides a method of manufacturing a GlgE inhibitor, the method comprising screening for a putative antibacterial by any of the methods disclosed herein, preparing the putative antibacterial, and purifying the putative antibacterial. The present invention also provides a method of manufacturing a Rv3032 inhibitor, the method comprising screening for a putative antibacterial by the method of any of the methods disclosed, preparing the putative antibacterial, and purifying the putative antibacterial.

The present invention further provides a pharmaceutical composition comprising a GlgE inhibitor in a pharmaceutically acceptable carrier. The present invention additionally provides a pharmaceutical composition comprising a Rv3032 inhibitor in a pharmaceutically acceptable carrier.

DETAILED DESCRIPTION OF THE INVENTION

Figure 1A:
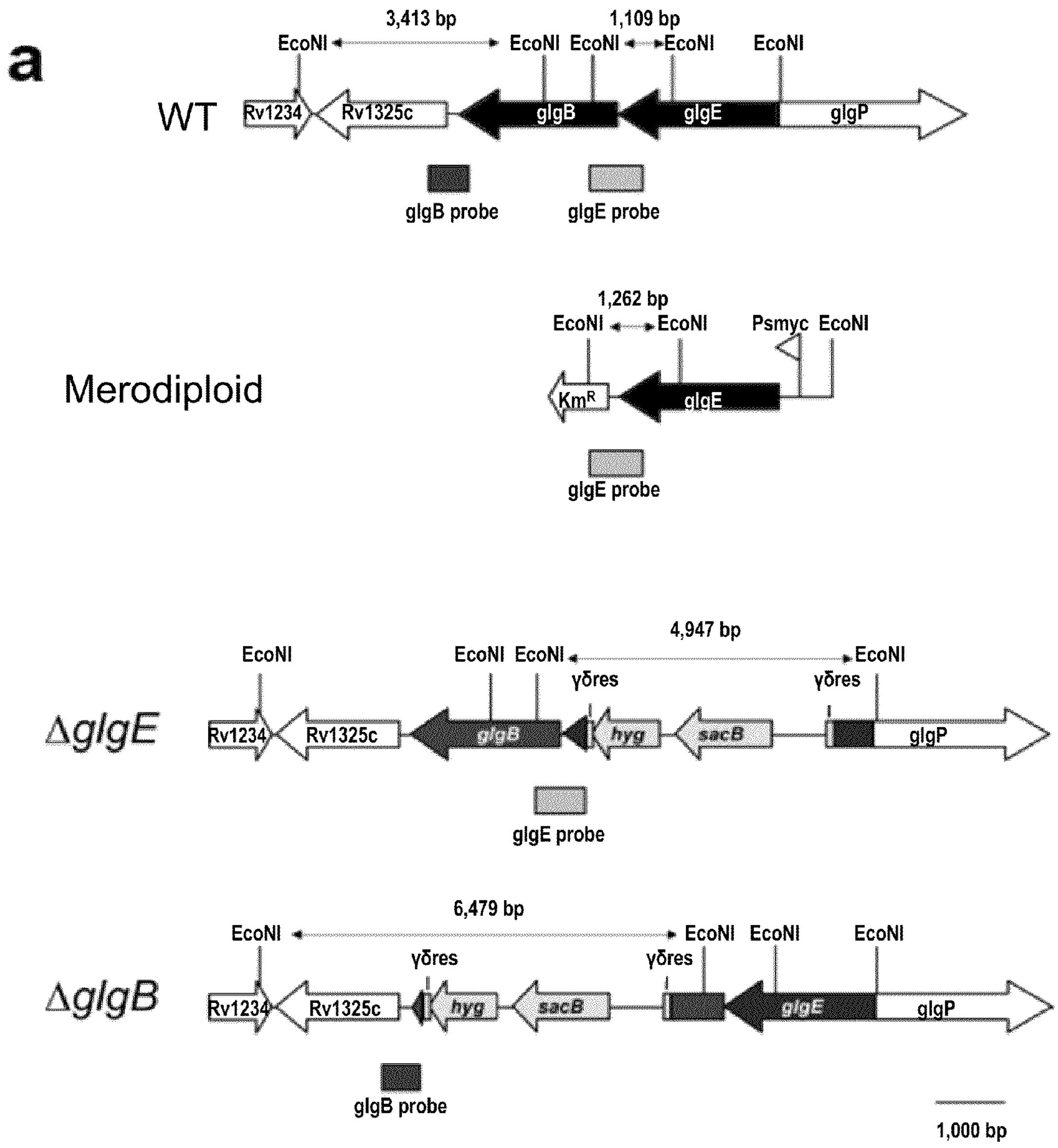
FIG. 1A-1D. Proving the essentiality of glgE in Mtb. (A) Organization of the glgE and glgB gene loci in Mtb WT, the glgE merodiploid, and the ΔglgE and ΔglgB mutants. (B) Southern analysis of EcoNI-digested genomic DNA from merodiploid mutant strains using a glgE probe as indicated in (A), showing deletion of glgE in the merodiploid strain. Suppressing essentiality of glgE (C) and glgB (D) in Mtb by inactivation of treS. Southern analysis of EcoNI-digested genomic DNA from double mutant strains using a glgE or glgB probe as indicated in (A), showing deletion of glgE or glgB in the ΔtreS mutant.

The present invention provides a method for determining whether an agent is a putative antibacterial, the method comprising determining whether or not the agent inhibits GlgE, wherein an agent that inhibits GlgE is a putative antibacterial. An agent that inhibits GlgE will be lethal to a bacterium and therefore, is an antibacterial.

GlgE (Rv1327c) is a glucosyltransferase involved in glycogen metabolism. It is involved in the TreS-Pep2-GlgE-GlgB metabolism pathway, a major α-glycan synthesis route. GlgE is present in a majority of bacteria such as mycobacteria and opportunistic pathogens such as those from the genus *Pseudomonas* and *Burkholderia*. There is no glgE eukaryote homologue, making GlgE an attractive drug target. GlgE forms linear α-1,4-glucan from maltose 1-phosphate (M1P) and edits branch lengths of branched glucans.

Inhibition of GlgE in bacteria results in a buildup of M1P since GlgE can not metabolize M1P into α-1,4-glucan. This results in lethal concentrations of M1P within the cell, causing bacterial cell death. Many bacteria metabolize all carbon sources, such as saccharides, via the TreS-Pep2-GlgE-GlgB pathway by first producing trehalose from the other carbon sources. Therefore, in some such bacteria, inhibition of GlgE will lead to toxic buildup of M1P and cell death when the cells are in the presence of any carbon source. In other bacteria however, the amount of trehalose produced from other carbon sources is too low to result in a toxic buildup of M1P when GlgE is inhibited. The carbon source may be either organic, such as a saccharide, or inorganic, such as carbon dioxide. Examples of such bacteria include, but are not limited to *M. tuberculosis, M. bovis*, and *M. bovis* BCG. Some bacteria utilize the TreS-Pep2-GlgE-GlgB pathway only to metabolize the organic carbon source trehalose. Inhibition of GlgE in those bacteria will only result in cell toxicity in the presence of trehalose.

GlgE can be inhibited directly by blocking the binding sites, denaturing, or changing confirmation of GlgE, or indirectly such as by using a carbon source lacking a non-reducing 4-hydroxy group. Non-limiting examples include 4-hydroxyl group are 4-deoxytrehalose and 4-deoxymaltose. Upon metabolism by GlgE, the carbon source lacking the non-reducing 4-hydroxyl group results in an α-glucan without a 4-hydroxyl non-reducing end, leading to chain termination of the α-glucan. Since GlgE is a transferase with M1P as the donor and an α-glucan as an accepter, when there is no suitable acceptor, such as when there is chain termination of the α-glucan, GlgE can not metabolize M1P. This indirect inhibition of GlgE activity results in a buildup of M1P in the cells, leading to cell toxicity.

GlgE may also be indirectly inhibited by inhibition of GlgB. GlgE produces linear α-1,4-glucans that have few non-reducing ends and which become insoluble once they reach a degree of polymerization (DP) ~20. GlgB produces branches glucans from the linear products of GlgE. When GlgB is inhibited, GlgE is inhibited due to the low number of non-reducing ends which can function as acceptors. This results in a toxic buildup of M1P in the cell. GlgB activity can be measured by any method known in the art such as assays based on debranching followed by chromatography, MS, or capillary electrophoresis after derivatisation.

Inhibition of TreS or Pep2 may also result in indirect inhibition of GlgE by, for instance, changing the presence of non-reducing groups or the steric chemistry of GlgE's substrate.

One method of determining whether a putative antibacterial inhibits GlgE comprises contacting GlgE with the putative antibiotic in the presence of maltose 1-phosphate and maltooligosaccharide, and measuring GlgE activity. The activity of GlgE can be measured by measuring the release of inorganic phosphate from M1P. GlgE takes M1P and α-1,4-$glucan_n$ as a substrate, with α-1,4-$glucan_{n+2}$ and inorganic phosphate as products (n=number of glucose units). Release of inorganic phosphate can be measured by any method known in the art including, but not limited to, malachite green colorimetric detection. Another way of determining whether a putative antibacterial inhibits GlgE comprises contacting GlgE with the putative antibacterial in the presence of maltose 1-phosphate and maltooligosaccharide and measuring maltooligosaccharide elongation or maltose 1-phosphate consumption. GlgE metabolism of maltose 1-phosphate results in an elongation of maltooligosaccharide. GlgE activity can be quantitatively measured via matrix-assisted laser desorption/ionization (MALDI) mass spectrometry or chromatography such as thin layer chromatography measuring maltooligosaccharide elongation or maltose 1-phosphate depletion, or any other method of measurement known in the art. Additionally, GlgE disproportionation activity can be measured by any method known in the art including, but not limited to, chromatography or mass spectrometry. As a control, the activity of GlgE in the presence of M1P or M1P and maltooligosaccharide, but in the absence of the putative antibacterial can be measured.

Rv3032 is a glucosyltransferase involved in another glycogen metabolism pathway. Rv3032 utilizes either UDP-glucose or ADP-glucose to polymerize linear α-1,4-glucan. On its own, inhibition of Rv3032 is not lethal. However, when the glycogen metabolism TreS-Pep2-GlgE-GlgB pathway is inactivated, inhibition of Rv3032 leads to cell death. The glycogen metabolizing TreS-Pep2-GlgE-GlgB pathway can be inactivated by rendering TreS or Pep2 inoperable. When TreS or Pep2 is inoperable, formation of M1P is blocked. Since cells with inoperable TreS or Pep2 can not form M1P, the cells can be grown in any medium, including those with trehalose. A putative antibacterial that inhibits Rv3032 will be synthetically lethal to bacteria, and can be used in conjunction with other treatment to achieve bacterial lethality. Using an Rv3032 inhibitor in conjunction with other treatment can help overcome bacterial drug resistance or delay or frustrate gain-of-function mutations by bacteria. Rv3032 may be indirectly inhibited by inhibiting Rv3031 or Rv3030, enzymes in the Rv3032 glycogen metabolism pathway. Inhibition of Rv3031 or Rv3030 may inhibit Rv3032 by, for example, altering Rv3032's substrate.

A method of determining whether a putative antibacterial inhibits GlgE or Rv3032 comprises contacting bacterial cells with the putative antibacterial and measuring GlgE or Rv3032 activity. GlgE or Rv3032 activity may be measured by any method known in the art, including but not limited to glucosyltransferase assays such as pH-stat assays and assays employing whole cell extracts or purified protein. As a control, glucosyltransferase activity in bacterial cells which were not contacted with the putative antibacterial can be measured by any method known in the art including, but not limited to, glucosyltransferase assays employing whole cell extracts or purified protein.

Another method for determining whether a putative antibacterial inhibits GlgE or Rv3032 comprises contacting bacterial cells with the putative antibacterial and measuring cellular carbohydrates. Inhibition of GlgE or Rv3032 will result in changes in cellular carbohydrate composition. As a control, cellular carbohydrates of cells that utilize GlgE in glycogen metabolism can be measured. This analysis can be done by any method known in the art, including but not limited to, thin layer chromatography analysis.

The analysis of GlgE activity or cellular carbohydrates is preferably performed after sufficient time has elapsed to allow, under conditions of optimal growth, to allow GlgE to catalyze M1P polymerization and result in a measurable release of phosphates, a measurable amount of maltooligosaccharide elongation, or a measurable change in cellular carbohydrate composition. This time period is between 30 seconds and 24 hours. Changes are relative to controls.

A method of determining whether a putative antibacterial inhibits GlgE comprises contacting bacterial cells with the putative antibacterial and measuring cell viability.

In order to determine the efficacy of a putative antibacterial, cell viability is measured sufficient time after contacting the bacterial cells with the putative antibacterial which would, under conditions of optimal cell growth, provide sufficient time for multiple cell division cycles to occur. This period is between 24 and 192 hours. When the bacterial cells are cultivated in vitro, it is preferably between 36 and 60 hours. When the bacterial cells are in vivo, such as in a rodent, it is preferably between 150 and 180 hours. Cell growth in a control is measured after the passage of the same amount of time. Conditions of optimal growth include the absence of external stressors, such as putative antibacterials.

Cell viability can be measured by any method known in the art. For example, cell viability can be measured by, among other techniques, measurement of the optical density of cultures or measurement of colony forming units. A statistically significant reduction in measurement of viability in those cells exposed to the putative antibacterial versus control cells signifies that the putative antibacterial is an antibacterial candidate.

One or more controls may be used in order to ascertain whether there has been a statistically significant difference in the cell growth of those cells contacted with the putative antibacterial. The control may comprise one or more of the following: (1) measuring viability of bacterial cells in the absence of the putative antibacterial; (2) contacting bacterial cells with the putative antibacterial in the absence of trehalose, and measuring cell viability; and (3) contacting bacterial cells that have inoperable TreS or Pep2 with the putative antibacterial, and measuring cell viability. When the bacterial cells being used utilize the TreS-Pep2-GlgE-GlgB pathway only in the presence of the disaccharide trehalose, absence of trehalose in the control will preclude buildup of M1P, even in the presence of a GlgE inhibitor. TreS and Pep2 are enzymes in the TreS-Pep2-GlgE-GlgB metabolism pathway which produce M1P. A cell that has either inoperable TreS or inoperable Pep2, or where both enzymes are inoperable, can not produce M1P, and therefore inhibition of GlgE will not result in a toxic buildup of M1P. TreS or Pep2 can be made inoperable in a cell by mutation of the gene for TreS or Pep2, or by inhibition of TreS or Pep2. Mutation can be done by any method known in the art, such as by deletion or substitution, and can be heterozygous or homozygous. Preferably, the mutation of TreS or Pep2 results in absence or inoperability of the TreS or Pep2 enzyme. Alternatively, TreS or Pep2 can be rendered inoperable by the addition of an inhibitor for TreS or Pep2. The inhibitor used to inhibit TreS or Pep2 can be any known in the art, including, but not limited to, validamycin A to inhibit TreS.

The present invention provides a method for determining whether an agent is a putative antibacterial, the method comprising determining whether or not the agent inhibits Rv3032, wherein an agent that inhibits Rv3032 is a putative antibacterial. A Rv3032 inhibitor causes synthetic lethality and, when used in conjunction with other treatment, is lethal to bacterial cells.

One method of determining whether a putative antibacterial inhibits Rv3032 comprises contacting bacterial cells having inoperable TreS or Pep2 with the putative antibacterial and measuring cell viability. A cell with inoperable TreS or Pep2 will not be able to utilize the TreS-Pep2-GlgE-BlgB glycogen metabolism pathway. Although such cells are viable, as are cells with inhibited Rv3032 but operable TreS-Pep2-GlgE-GlgB glycogen metabolism pathway, inhibition of Rv3032 in cells with inoperable TreS or Pep2 is synthetically lethal. Cell viability can be measured by any method known in the art, including but not limited to, colony forming units or whole cell count.

The putative antibacterial in the present invention can be any chemical or biological agent such as a chemical, small compound, polypeptide, saccharide, protein, protein fragment, or aptamer. Preferably, the putative antibacterial is membrane-permeable. Most preferably, the putative antibacterial is not toxic to eukaryotic cells. An aptamer may be a single stranded oligonucleotide or oligonucleotide analog that binds to a particular target molecule, such as a protein. Preferably, the saccharide is a saccharide lacking a non-reducing 4-hydroxyl group, for example, 4-deoxytrehalose or 4-deoxymaltose.

The cells can be any bacteria. Preferably, the cell is a mycobacteria or an opportunistic pathogen. *Mycobacteria* include, but are not limited to all strains, including drug resistant strains of, *M. tuberculosis, M. bovis, M. bovis* BCG, *M. smegmatis, M africanum, M. canetti, M. caprae, M. microti, M. pinnipedii, M. avium, M. avium paratuberculosis, M. avium silvaticum, M. avium "hominissuis," M. colombiense, M. asiaticum, M. gordonae, M. gastri, M. kansaii, M. hiberniae, M. nonchromogenicum, M. terrae, M. triviale, M. ulcurans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookie, M. celatum, M. bohemicum, M. haemophilum, M. malmoense, M. szulgai, M. leprae, M. lepraemurium, M. lepromatosis, M. botniense, M. chimaera, M. conspicuum, M. doricum, M. farcinogenes, M. heckeshornense, M. intracellulare, M. lacus, M. marium, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. fortuitum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. goodie, M. wolinskyi, M. thermoresistabile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. bolletii, M. caprae, M. chlorophenolicum, M. fluoroanthenivorans, M. kumamotonense, M. novocastrense, M. parmense, M. phocaicum, M. poriferae, M. rhodesiae, M. seoulense*, and *M. tokaiense*. Opportunistic pathogens may be from genus *pseudomonas* or genus *burkholderia. Pseudomonas* include, but are not limited to, *P. aeruginosa, P. oryzihabitans, P. syringae, P. tolaasii, P. agarici*, and *P. plecoglossicida. Burkholderia* include, but are not limited to, *B. mallei, B. pseudomallei*, and *B. cepacia*. When using the methods or assays of the present invention, a preferred cell is *M. smegmatis* since it is fast-growing and not harmful to humans. When using the methods or assays of the present invention in order to determine putative antibacterials of other bacteria, *M. smegmatis* may be used instead. Alternatively, mutant glgE *M. smegmatis* cells can have glgE from the bacteria of interest added. This will result in *M. smegmatis* with the same glgE as the bacteria of interest. Preferably, glgE sequence is deleted from *M. smegmatis* before adding the glgE sequence from the bacteria of interest. The glgE sequence from the cells of interest can be added to the *M. smegmatis* by any method known in the art, such as transfection.

The present invention provides an antibacterial identified by a method comprising (1) determining whether a putative antibacterial inhibits GlgE or Rv3032 by measuring GlgE or Rv3032 activity, or (2) determining whether a putative antibacterial inhibits GlgE by measuring cell viability. GlgE activity, Rv3032 activity, and bacterial cell viability can be determined by any of the methods described above.

The present invention provides a method of treating a subject infected with a bacterium, the method comprising administering to the subject a GlgE inhibitor in an amount effective to treat the bacterial infection. The present invention also provides a method of treating a subject infected with a bacterium, the method comprising administering to the subject a GlgE inhibitor and a Rv3032 inhibitor in an amount effective to treat the infection.

The subject may be any eukaryote, such as a mammal or a plant. Preferably, the subject is a mammal, such as a rodent. Most preferably, the subject is a human.

Treating a subject's bacterial infection means curing, ameliorating, or minimizing the clinical manifestations or symptoms of the subject's bacterial infection. For example, when the subject is infected with Mtb, treating the subject involves the administration of GlgE inhibitor or GlgE and Rv3032 inhibitors sufficient to cure, ameliorate, or minimize the clinical manifestations of fever, dry cough, pleuritis, chest pains, fever, weight loss, weakness, loss of appetite, increased mucus production, night sweats, and the coughing up of blood. The amount of GlgE inhibitor or GlgE and Rv3032 inhibitors effective to treat the subject's bacterial infection will vary depending on the type of bacteria, the severity of the bacterial infection, the subject's condition, and the severity of the clinical manifestations and symptoms. Appropriate amounts of GlgE inhibitor or GlgE and Rv3032 inhibitors effective to treat the subject's bacterial infection can be readily determined by the skilled artisan without undue experimentation. The manner of administration of the GlgE inhibitor or the GlgE and Rv3032 inhibitors depends on the type and site of bacterial infection. According to the methods of the present invention, the GlgE inhibitor or the GlgE and Rv3032 inhibitors may be administered by any method known in the art, including but not limited to, oral or parenteral administration.

A trehalose enriched diet may increase the potency of the GlgE inhibitor being administered. Trehalose is a natural carbohydrate abundantly present in fungi and yeast derived food products and is a commercially available FDA approved food supplement, often used as a sucrose supplement. A trehalose enriched diet results in increased tissue levels of trehalose and is well tolerated in humans. Increased tissue levels of trehalose results in increased levels of toxic M1P when GlgE is inhibited.

The present invention provides a method of manufacturing or a GlgE inhibitor or a Rv3032, the method comprising screening for a putative antibacterial by the method of any the methods above, preparing the putative antibacterial, and purifying the putative antibacterial. The method of preparing and purifying the putative antibacterial will differ depending on the putative antibacterial being manufactured. The method of preparation or purification best resulting in the highest yield of the pure putative antibacterial can be determined by one of ordinary skill in the art without undue experimentation. Any method of preparation and purification known in the art can be used.

The present invention provides for a pharmaceutical composition comprising a GlgE inhibitor in a pharmaceutically acceptable carrier. The present invention also provides for a pharmaceutical composition comprising a GlgE inhibitor and a Rv3032 inhibitor in a pharmaceutically acceptable carrier. The pharmaceutically acceptable carrier used will depend on the method of administration as well as the subject to whom the pharmaceutical composition will be administered. Any pharmaceutically acceptable carrier known in the art can be used.

The GlgE inhibitor or Rv3032 inhibitor may be any putative antibacterial discussed herein. The GlgE inhibitor may be any trehalose, maltose or maltose 1-phosphate with a modified 4-position or 5-position including, but not limited to 4,4-dimethyl trehalose, 4-methyl trehalose, 4-deoxy trehalose, 4-deoxy-fluoro trehalose, 5-fluoro trehalose, 4,4-dimethyl maltose, 4-methyl maltose, 4-deoxy maltose, 4-deoxy-fluoro maltose, 5-fluoro maltose, 4-dimethyl maltose 1-phosphate, 4-methyl maltose 1-phosphate, 4-deoxy maltose 1-phosphate, 4-deoxy-fluoro maltose 1-phosphate, and 5-fluoro maltose 1-phosphate. Metabolism of these inhibitors by GlgE would result in an unsuitable receptor for further GlgE activity, leading to a buildup of M1P in the cell. Additionally, the GlgE inhibitor may be any trehalose with a modified 2-, 3-, or 6-position which inhibit GlgE activity on steric grounds.

For oral administration, the formulation of the GlgE inhibitor or Rv3032 inhibitor may be presented as capsules, tablets, powder, granules, or as a suspension. The formulation may have conventional additives, such as lactose, mannitol, corn starch, or potato starch. The formulation may also be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For a parenteral administration, the GlgE inhibitor or Rv3032 inhibitor may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be present in unit or multi-dose containers, such as sealed ampoules or vials. The formulation may be delivered by any mode of injection, including, without limitation, epifascial, intrasternal, intravascular, intravenous, parenchymatous, or subcutaneous.

EXPERIMENTAL DETAILS

1. Methods and Materials

Generation of gene deletion mutants. Mutants of *M. smegmatis* mc$^2$155 and Mtb H37Rv were generated by allelic exchange employing specialized transduction (30). Cells were grown aerobically at 37° C. in Middlebrook 7H9 media supplemented with 10% (v/v) OADC enrichment (Becton Dickinson Microbiology Systems, Spark, Md.), 0.5% (v/v) glycerol and 0.05% (v/v) Tyloxapol. Hygromycin (50 mg/l) and kanamycin (20 mg/l) were added for selection for appropriate strains. Validamycin A (VA) (Research Products International Corp., Mount Prospect, Ill.) was used at either 5 or 10 mM. for inhibiting TreS activity where indicated.

For generating the allelic exchange constructs designed to replace genes in *M. smegmatis* and Mtb with a γδres-sacB-hyg-γδres cassette comprising a sacB as well as a hygromycin resistance gene flanked by res-sites of the γδ-resolvase, upstream and downstream flanking DNA regions were amplified by PCR. Subsequently, the upstream and downstream flanks were digested with the indicated restriction enzymes, and ligated with Van91I-digested p0004S vector arms. The resulting knock-out plasmids were then linearized with PacI and cloned and packaged into the temperature-sensitive phage phAE159 as previously described (33), yielding knock-out phages. Allelic exchange in *M. smegmatis* and Mtb using the knock-out phages was achieved by specialized transduction as reported previously (33) using hygromycin (50 mg/l) for selection, resulting in gene deletion and replacement by the γδres-sacB-hyg-γδres cassette. For generation of unmarked mutants, the γδres-sacB-hyg-γδres cassette was removed employing specialized transduction using the phage phAE7-1 expressing the γδ-resolvase using sucrose (3%, w/v) for counterselection. The obtained marked and unmarked mutants were verified by Southern analysis of digested genomic DNA using appropriate restriction enzymes and [α-$^{32}$P]dCTP-labeled probes.

For recombinant gene expression in mycobacteria, the plasmid pMV361$^{Kan}$ (34) or the pMV361-derivative pTIC6a$^{Kan}$ were used. Genes were amplified by PCR using the oligonucleotide pairs 5'-TTTTTTAAGCTTGTGAG-GAGTGGTTGGGTGGCCGG-3' (SEQ ID NO:1) and 5'-TTTTTTATCGATTCATTCCCTGCGTAG-CAAGTCGAG-3' (SEQ ID NO:2) for glgE$_{Msmeg}$; 5'-TTTTT-TAAGCTTATGACGAGAAGCAGCAATCAACTC-3' (SEQ ID NO:3) and 5'-TTTTTTATCGATCTAAGCCG-GCTCGAACCAGAGCATC-3' (SEQ ID NO:4) for glgB$_{Msmeg}$; 5'-TTTTTTAAGCTTGTGAGTGGC-CGGGCAATCGGAAC-3' (SEQ ID NO:5) and 5'-TTTTTTGATATCTCACCTCCTGCGCAGCAGCGTG-3' (SEQ ID NO:6) for glgE$_{Mtb}$; and 5'-TTTTTTCAGCTG-CAATGAACGAGGCAGAACACAGCGTC-3' (SEQ ID NO:7) and 5'-TTTTTTAAGCTTCATAGGCGCCGCTCTC-CCCCGC-3' (SEQ ID NO:8) for treS$_{Mtb}$, cloned using the underlined restriction sites, and plasmids were transformed into mycobacteria by electroporation.

Carbohydrate TLC analysis. Carbohydrates were extracted from equal amounts of cells with hot water (95° C. for 4 hours) and analyzed by TLC on Silica gel 60 (EMD Chemicals) using the solvent system 1-propanol:ethyl acetate:water (6:1:3, v/v/v). For separation of trehalose and maltose, the solvent system n-butanol:pyridine:water (7:3:1, v/v/v) was used. $^{14}C$-α-D-trehalose (specific activity 300 mCi/mmol; American Radiolabeled Chemicals) was used in some experiments at a concentration of 0.1 μCi/ml. Substances were visualized by spraying TLC plates with 10% (v/v) sulfuric acid in ethanol followed by charring at 180° C. for 10 minutes, or by autoradiography where applicable.

Purification and assay of Mtb GlgE. The Mtb glgE gene was synthesized with optimized codon usage for expression in *E. coli* (Genscript Corporation), heterologously expressed with an N-terminal 6×His tag, and purified using nickel-affinity and gel filtration chromatographies. GlgE activity was monitored quantitatively by the release of inorganic phosphate using malachite green colorimetric detection (31). Initial rates ($v_0$/[E]) were measured by quenching 3 μl reaction aliquots in 97 μl of 1 M. HCl at time points from 0.5 to 8 minutes. The quenched reactions were incubated with 700 μl of malachite green assay solution for 20 minutes at 21° C. and the $OD_{630}$ was measured on a Perkin Elmer Lambda 18 spectrophotometer. The concentration of free inorganic phosphate was estimated from a standard curve. Reaction rates were linear over at least the first 4 minutes. Unless otherwise stated, the enzyme assay was done in 100 mM. Bis-Tris propane (pH 7.0) containing 50 mM. NaCl at 37° C. Acceptor preference was examined in triplicate using 40 mM. maltooligosaccharide, 1 mM. α-M1P, and 37.5 nM. Mtb GlgE.

MALDI mass spectrometry. For qualitative analyses of maltooligosaccharide elongation, GlgE assays were performed with 12.5 mM. α-M1P, 50 mM maltooligosaccharide, and 1.5 μM. Mtb GlgE. Aliquots (1 μl) of reaction mixtures were diluted 50-fold in $H_2O$, mixed 1:1 with saturated aqueous 2,5-dihydroxybenzoic acid, loaded (1 μl) onto a gold target plate, and dried under vacuum. Analysis was carried out on a PBS-II mass spectrometer using ProteinChip 3.0 software (Ciphergen Biosystems Inc.).

NMR linkage analysis. A reaction (25 μl) containing 20 mM. maltotetraose, 20 mM α-M1P, and 1.2 μM. Mtb GlgE was allowed to reach completion according to the phosphate release assay. The reaction was heated to 99° C. for 15 min, cooled, and diluted to 500 μl with $D_2O$. A control reaction without enzyme was also prepared. One-dimensional $^1H$ spectra were recorded on an AVANCE 600 with TCI cryoprobe at 600 MHz and 300 K and analyzed with Topspin 2.1 software (Bruker Biospin Ltd.). Spectra were acquired with presaturation to suppress the water peak.

DNA microarrays and qRT-PCR. Triplicate 10 ml cultures of the conditional lethal Mtb mutant strain ΔtreS ΔglgE (pMV361::treS) and of the vector control strain were grown to log-phase in the presence of 5 mM. VA to suppress M1P formation. Subsequently, cells were washed to remove the inhibitor. After 48 hours of depletion of VA, cells were harvested, resuspended in 1 ml Qiagen RNA Protect reagent (Qiagen) and incubated 4 hours at room temperature. RNA was isolated by bead beating in a Fast-Prep apparatus (MP Biomedicals) and using the Qiagen RNeasy kit according to protocol. Contaminating DNA was removed with the Ambion TURBO DNA-free kit (Applied Biosystems). DNA microarrays were obtained through the NIAID's Pathogen Functional Genomics Resource Center (PFGRC, funded by the Division of Microbiology and Infectious Diseases, NIAID, NIH, DHHS and operated by the J. Craig Venter Institute). cDNA probes were prepared as per PFGRC protocol SOP#M007 (http://pfgrc.jcvi.org/index.php/microarray/protocols.html). Cy3- and Cy5-labeled cDNA probes were hybridized according to PFGRC protocol SOP#M008 to 70-mer oligo DNA microarrays representing the complete *M. tuberculosis* genome (JCVI PFGRC *M. tuberculosis* v. 4). One of the 3 biological replicates was dye-flipped. Slides were scanned on a GenePix 4000A scanner (Molecular Devices). Images were processed with the TM4 software suite (32). TIGR Spotfinder was used to grid and quantitate spots. TIGR MIDAS was used for Lowess normalization, standard deviation regularization, and in-slide replicate analysis with all quality control flags on and one bad channel tolerance policy set to generous. Results were analyzed in MeV with Significance Analysis of Microarrays (SAM) considered significant at $q<0.05$. Microarray data have been deposited in the NCBI Gene Expression Omnibus (GEO Series accession number GSE18575).

For qRT-PCR, the DNA-free RNA samples used for the microarray experiments were reverse transcribed with the SuperScript III First-Strand Synthesis System (Invitrogen). For the real-time reaction, each primer (250 nM) and 7.5 μl of template reaction (1:20 dilution) in 25 μl volume with Power SYBR Green PCR master mix (Applied Biosystems) was used. Triplicate samples were run on an ABI 7900 HT quantitative thermocycler. Threshold cycles were normalized to those for 16S rRNA.

Animal infections. BALB/c mice (4- to 6-week-old females; National Cancer Institute, Bethesda, Md.) were infected intravenously through the lateral tail vein at the indicated doses with exponentially growing Mtb strains suspended in 200 μl PBS containing 0.05% (v/v) Tween 80. At different time points, 3 mice per group were sacrificed, and bacterial burden was determined by plating serial dilutions of lung and spleen homogenates onto Middlebrook 7H10 agar plates supplemented with 10% (v/v) OADC enrichment (Becton Dickinson Microbiology Systems) and 0.5% (v/v) glycerol. Plates contained 5 mM VA for the conditional lethal Mtb mutant strain ΔtreS ΔglgE (pMV361::treS). Mouse protocols were approved by the Animal Care and Use Committee of the Albert Einstein College of Medicine.

Chemical analyses of maltose 1-phosphate isolated from *M. smegmatis* ΔglgE. For analysis of the monomer composition, carbohydrates were hydrolysed, reduced and acetylated according to reference 35. Gas chromatography (GC) of the alditol acetate derivative of the monosaccharides was performed using a TRACE 2000 series model (ThermoFinnigan, Herts, United Kingdom) equipped with a flame ionisation detector and a J & W DB-225 column (30 m×0.25 mm) (Agilent Technologies, South Queensferry, United Kingdom).

Electro spray ionization-mass spectrometry (ES-MS) was done in the negative ion mode using a Micromass/Waters LCT time of flight mass spectrometer (Waters Ltd., Elstree, United Kingdom) with methanol as the mobile phase.

The $^1H$ and $^{13}C$ data were recorded on a Bruker DRX-500 (Bruker Biospin Ltd., Coventry, United Kingdom) operating at 500.13 MHz for 1H and 125.77 MHz for 13C. The instrument was equipped with a 5-mm $^1H$-{$^{13}C$}-{X}-triple broadband inverse triple resonance z-gradient probe head and all spectra were run at 318 K (+45° C.). $D_2O$ was used as solvent and lock and referenced to an external capillary of TSP at 0 ppm (TSP is the sodium salt of trimethylsilylpropionic acid-d4, dissolved in $D_2O$). Data were acquired and processed using Bruker's XWINNMR version 2.6 software on a Silicon Graphics work station. All two-dimensional NMR data were acquired non-spinning. Data points (2048) were used in acquisition for the fast domain (F2) and 512 points were used in the incremental domain (F1). The F1 dimension was zero-filled to 1024 data points in processing. Eight transients per increment were employed. The gradient COSY-90 data was acquired with partial CW presaturation of the residual $D_2O$ signal during relaxation delay period. The data were transformed using a magnitude calculation and a non-shifted sine bell window function was used in both frequency domains in processing. The gradient HMBC data was transformed using a magnitude calculation and a Qsine window function shifted by π/2 was used for both frequency domains in processing. The gradient HSQC experiment was acquired in phase-sensitive mode using the time proportional phase increment. A Qsine window function shifted by π/2 was used for both frequency domains in processing. GARP decoupling was employed in the F1 domain for the HSQC experiment.

The $^{31}P$ data were recorded on a Bruker AV-300 operating at 121.46 MHz for $^{31}P$. The instrument was equipped with a 5 mm QNP (for computer switching between $^{1}H$ and $^{13}C$, $^{31}P$ and $^{19}F$) and which was also equipped with a z-gradient coil. The data was recorded at 300 K (+27° C.). $D_2O$ was used as solvent and lock. The $^{31}P$ reference used was orthophosphoric acid ($H_3PO_4$) in $D_2O$ at 0 ppm initially as an internal reference in a separate experiment, and then by using the corresponding SR value that this yielded. The $^{31}P$ spectrum was recorded with $^{1}H$ decoupling (WALTZ16). A line broadening of $^{1}H_3$ with an exponential multiplication window was used in processing.

Recombinant Mtb GlgE Production. The Mtb glgE gene was synthesized with optimized codon usage for expression in *Escherichia coli* (Genscript Corporation, Piscataway, N.J.), allowing expression of GlgE with a 6×His tag and a TEV cleavage site at its N-terminus. The construct was ligated into a pET21a expression vector (Novagen, Darmstadt, Germany) using NdeI and BamHI restriction sites. *E. coli* BL21(DE3) Star (Novagen) bearing this plasmid were grown at 25° C. to an $OD_{600}$ of 0.6 and expression was induced with 0.5 mM. isopropyl β-D-thiogalactopyranoside. Bacteria were harvested and lyzed after a further 16 hour incubation. The enzyme was purified using a 1 ml HisTrap FF column (GE Healthcare, Amersham, United Kingdom) with imidazole gradient elution and an S200 16/60 gel filtration column (Pharmacia Biotech, Amersham, United Kingdom) with 100 mM. Bis-Tris propane buffer, pH 7.0, containing 50 mM. NaCl. GlgE-containing fractions were pooled and concentrated to 0.5 mg/ml and aliquots were stored at −80° C.

2. Results

Validation of the Essentiality of glgE (Rv1327c) in Mtb H37Rv

Analysis of the function of essential genes could define novel drug target candidates for the treatment of XDR-TB strains. One such candidate, glgE (Rv1327c), has been predicted to be essential for in vitro growth of Mtb based on a genome-wide screen of a saturated transposon mutant library (2). The glgE homologue was also suggested to be essential in *M. smegmatis* (6). In addition to its presumed essentiality, GlgE fulfills further criteria for an excellent drug target; GlgE homologues are absent from humans as well as from commensal gut flora bacteria, but are present in almost all mycobacteria as well as in some opportunistic pathogens such as *Pseudomonas* and *Burkholderia* species.

Figures 1B, 1C, 1D:
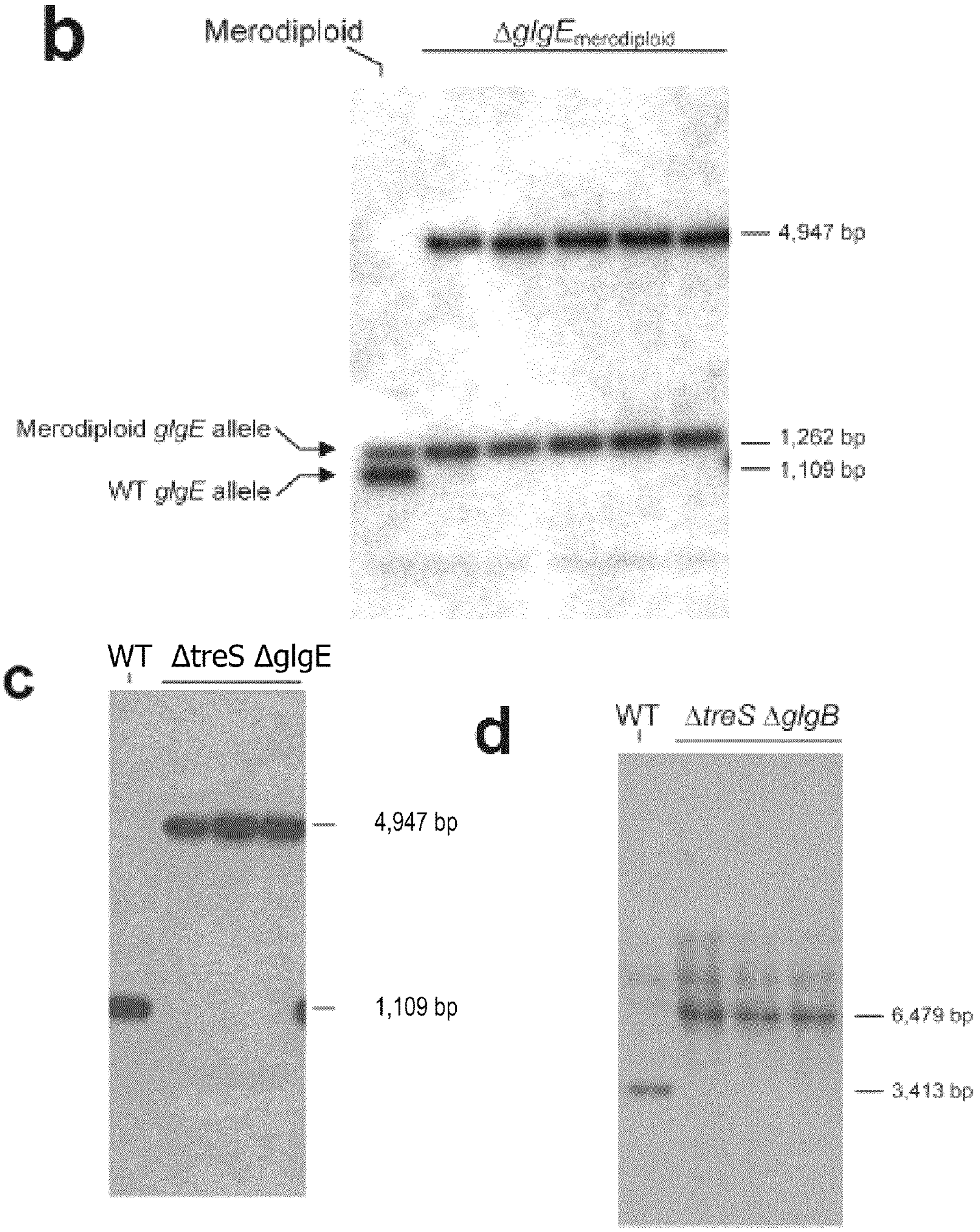

To verify the essentiality of glgE in Mtb, the frequencies of generating glgE deletion mutations in the wild type (WT) were compared to those in an isogenic merodiploid strain containing a second copy of glgE provided on an integrative single-copy plasmid, using specialized transduction. Transductants with a deleted WT allele were obtained only in the merodiploid but not in the haploid strain, thus rigorously confirming glgE essentiality in Mtb (FIGS. 1A, 1B).

Deletion of glgE in *M. smegmatis* mc²155 Results in Accumulation of Maltose 1-Phosphate Since glgE is clustered with genes coding for enzymes with known involvement in glycogen metabolism, such as the branching enzyme GlgB and the glycogen phosphorylase GlgP (FIG. 1A), and since GlgE resembles α-amylases, it has been proposed that GlgE is involved in glycogen degradation. The demonstration that thermal inactivation of GlgE in a temperature-sensitive *M. smegmatis* mutant strain apparently leads to increased glycogen accumulation (an α-1,4 glucan homopolysaccharide containing α-1,6-branches) and unexpected cell toxicity was interpreted as supporting the hypothesis that GlgE was a mediator of glycogen degradation (6). However, since high glycogen levels are not usually found to be toxic to bacteria, and since many bacteria capable of synthesizing and remobilizing glycogen do not possess a glgE orthologue, an alternative explanation was sought for the gene essentiality and unexpected cell toxicity.

Figures 2A, 2B, 2C, 2D:
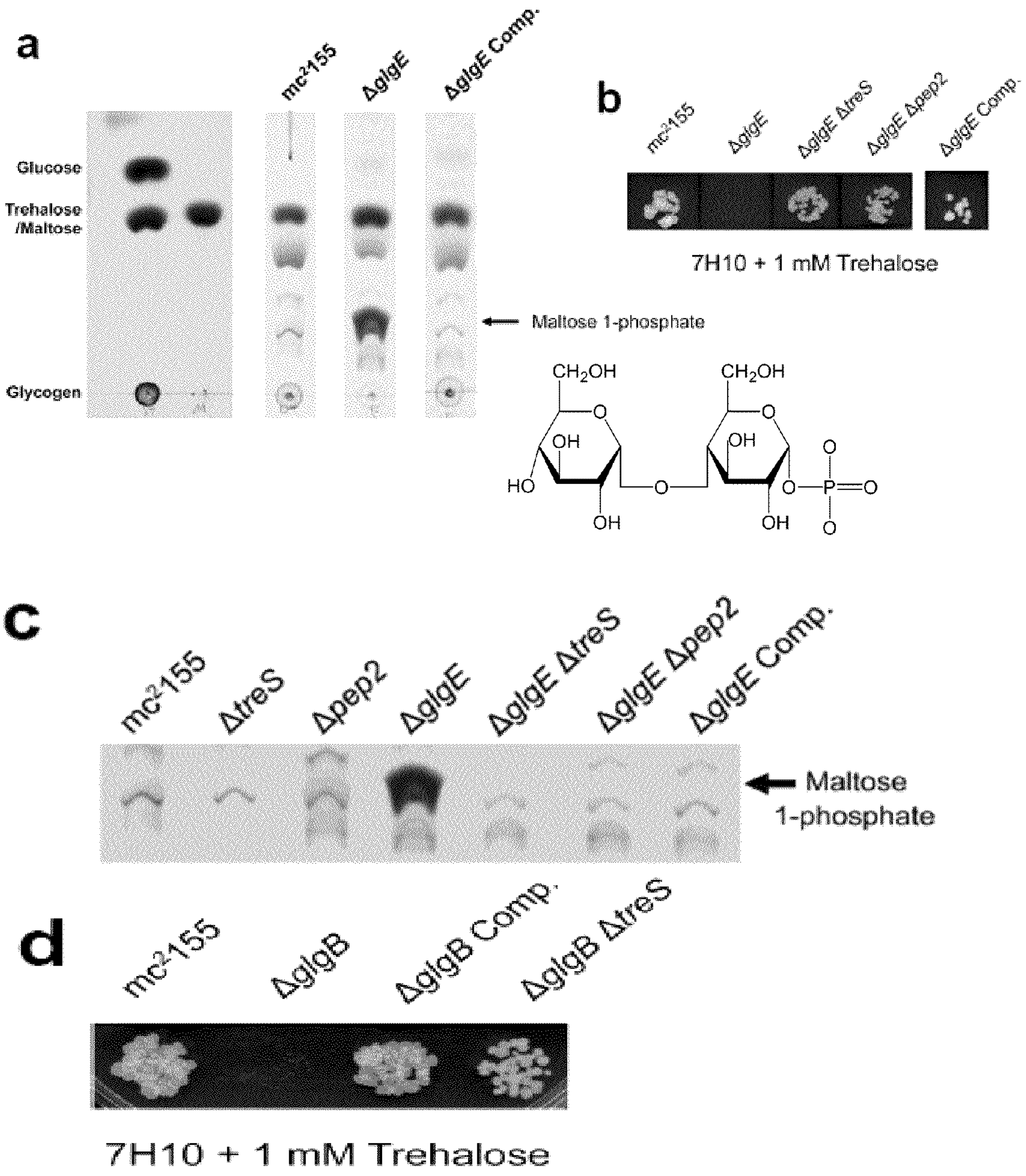
FIG. 2A-2F. Characterization of the *M. smegmatis* ΔglgE mutant. (A) M1P accumulation in the ΔglgE mutant, as revealed by TLC analysis of cell extracts from 48 hours old cultures. (B). Trehalose sensitivity of the ΔglgE mutant. (C) Abolition of M1P accumulation by suppressor mutations in the ΔglgE mutant, as revealed by TLC analysis of cell extracts from 48 hours old cultures. (D) Trehalose sensitivity of the ΔglgB mutant. (E) M1P accumulation in the ΔglgE and ΔglgB mutants determined by TLC/autoradiography analysis of extracts from cells labeled with 14C-trehalose for the indicated time intervals. (F) Maltose accumulation in Δpep2 mutant strains determined by TLC/autoradiography analysis of cell extracts from cells labeled with 14C-trehalose for 30 min. In (B) and (D), equal dilutions of cultures were spotted onto Middlebrook 7H10 agar plates containing trehalose. Comp. refers to mutants complemented with the respective WT genes.

In order to reexamine GlgE function, deletion of the glgE homologue in *M. smegmatis* was attempted by specialized transduction. In contrast to GlgE's suggested essentiality (6), null deletion mutations could be readily generated on a minimal medium, allowing biochemical characterization of the function of the GlgE protein. Thin layer chromatography (TLC) analysis of hot water extracts from the *M. smegmatis* ΔglgE mutant revealed no increased glycogen content, but copious amounts of a low-molecular weight carbohydrate (FIG. 2A). This substance was purified by size exclusion chromatography followed by preparative TLC, and subjected to various chemical analyses, including NMR spectroscopy and electron spray ionization-mass spectrometry, as well as gas chromatography of the alditol acetate derivative. In combination, these analyses identified the substance as α-D-glucopyranosyl(1→4)-α-D-glucopyranosyl 1-phosphate (maltose 1-phosphate, M1P). To quantify glycogen in the temperature-sensitive glgE mutant, a coupled enzymatic reaction that measures glucose released upon amyloglucosidase treatment of extracted polysaccharides was used (6). Since amyloglucosidase has no molecular weight specificity, the coupled assay would not have discriminated between M1P and glycogen, leading to a likely misinterpretation.

Suppressor Mutations of Trehalose-Induced Bacteriostasis Establish a Functional Link Between GlgE, GlgB, TreS, and Pep2 in *M. smegmatis* mc² 155

Surprisingly, although the *M. smegmatis* ΔglgE mutant grew normally in minimal medium (Middlebrook 7H9), it could not grow in complex media (e.g., Luria-Bertani (LB) broth). To identify the growth-inhibitory component(s) in LB broth, the sensitivity of the *M. smegmatis* ΔglgE mutant toward various mono- and disaccharides was tested, and it was found to be sensitive to the disaccharide trehalose [α-D-glucopyranosyl-(1→1)-α-D-glucopyranoside]. This is surprising since this sugar is abundant in mycobacteria and yet a concentration of 0.5 mM. completely inhibited growth of the mutant (FIG. 2B). The sensitivity was highly specific, since growth of the mutant was not inhibited by other glucose disaccharides like maltose or α,β-trehalose [α-D-glucopyranosyl-(1→1)-β-D-glucopyranoside]. Trehalose induced a bacteriostatic growth arrest in *M. smegmatis* ΔglgE which correlated with M1P hyperaccumulation.

Spontaneous mutations restoring growth of *M. smegmatis* ΔglgE in the presence of trehalose were observed at a frequency of $4.5\times10^{-5}$. In order to identify the presumed suppressor mutations that abolished trehalose sensitivity, a transposon mutant library of *M. smegmatis* ΔglgE was screened by selecting for resistance to 1 mM. trehalose. Mapping of the transposon insertion sites in trehalose-insensitive ΔglgE mutants identified the trehalose synthase gene treS (Rv0126 homologue) as a target in several independent clones. In order to confirm the transposon mutant phenotypes, treS was deleted in an unmarked *M. smegmatis* ΔglgE strain by specialized transduction. Additionally, pep2 gene (Rv0127 homologue), which is clustered with treS in many bacteria, was separately deleted. Both second-site gene deletions conferred trehalose resistance and suppressed M1P accumulation caused by glgE inactivation (FIGS. 2B, 2C).

Figures 2E, 2F:
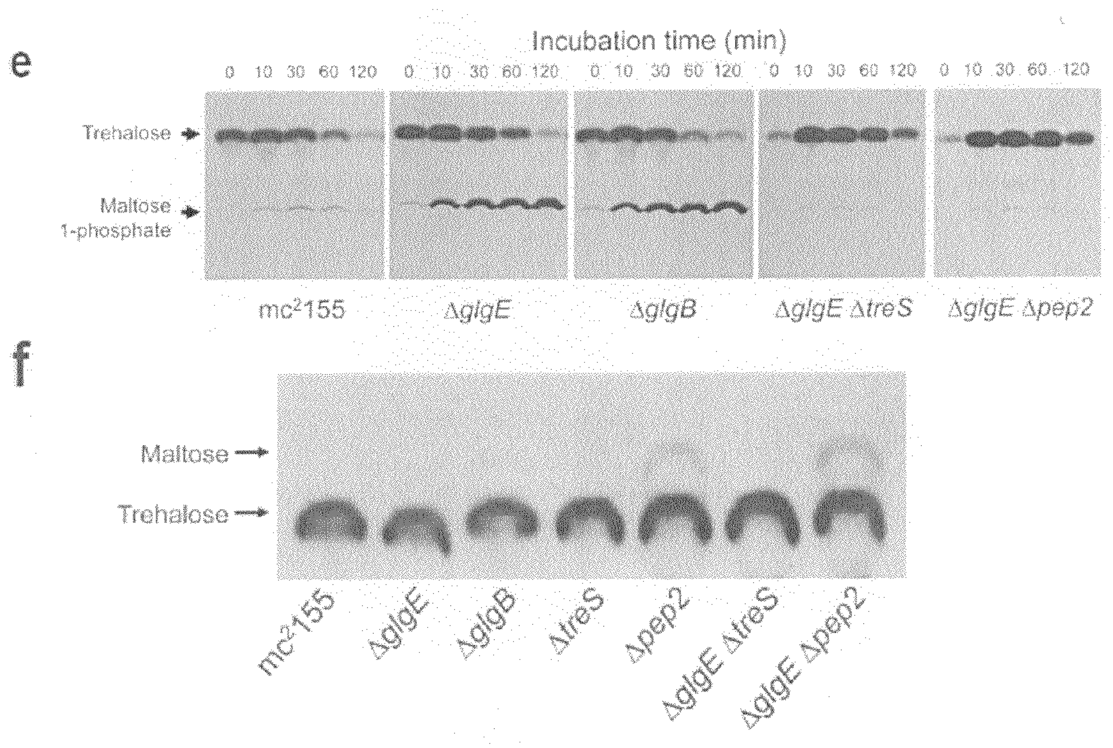

The glgB gene (Rv1326c) clusters with glgE and encodes a branching enzyme, required for introducing α-1,6-linked branches into linear α-1,4-glucans (7), which has recently been demonstrated to be essential in Mtb H37Rv (8). GlgB was found to be nonessential in *M. smegmatis* mc$^2$155. Moreover, the *M. smegmatis* ΔglgB mutant was also sensitive to trehalose, although to a somewhat smaller extent than ΔglgE. Trehalose sensitivity in an unmarked *M. smegmatis* ΔglgB strain could again be suppressed by deletion of treS (FIG. 2D). Trehalose synthase (TreS) mediates the reversible interconversion of trehalose and maltose (9, 10). Pep2 from Mtb has not been characterized but is homologous to a maltokinase Mak1 from phylogenetically related actinomycetes (*Actinoplanes* and *Streptomyces*), that phosphorylates maltose to M1P using ATP (11). The clustering of treS and pep2 thus suggests that M1P is synthesized from trehalose via maltose by sequential reactions mediated by TreS and Pep2. To corroborate this, *M. smegmatis* mutant strains were labeled with $^{14}$C-trehalose (FIG. 2E). Radiolabeled trehalose was rapidly taken up and metabolized to M1P in the ΔglgE mutant. Also, glgB deletion led to a rapid accumulation of M1P, whereas this phosphosugar never reached high levels in the WT. Inactivation of treS or pep2 prevented M1P formation in the ΔglgE mutant. Substantial levels of the radiolabeled maltose intermediate were detectable only in Δpep2 strains, indicating its usual fast turnover to M1P by Pep2 (FIG. 2F). Together, these findings establish a functional link among TreS, Pep2, GlgE, and GlgB in *M. smegmatis*. This is supported by the fact that the structural genes, while arranged in two separate chromosomal gene clusters in mycobacteria, often lie in a single locus in many other prokaryotes.

GlgE is a Novel Maltosyltransferase Utilizing M1P as its Donor Substrate

Figures 3A, 3B:
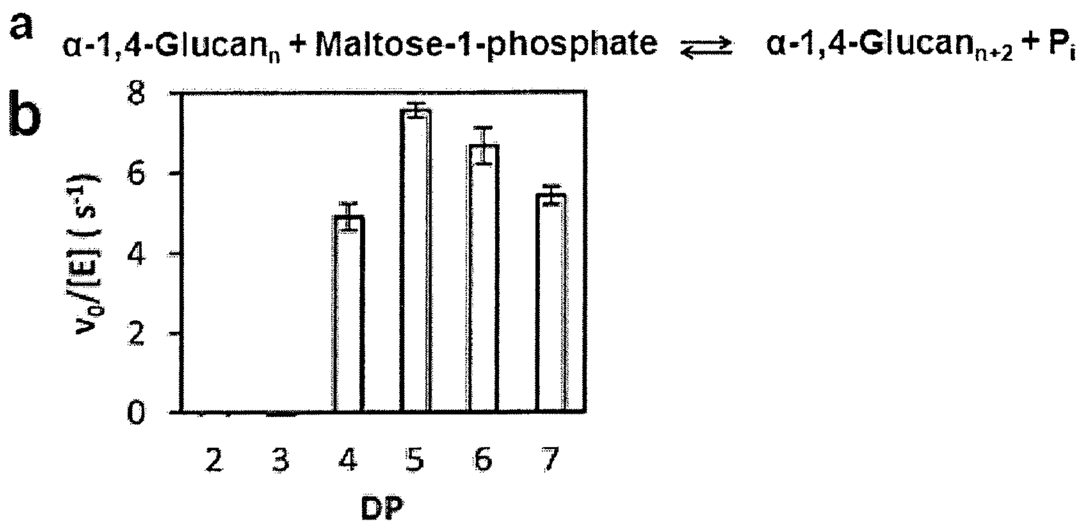
FIG. 3A-3F. GlgE is a novel M1P-dependent maltosyltransferase. (A) Proposed reaction catalyzed by GlgE. (B) Acceptor specificity of Mtb GlgE. Enzyme activity with maltooligosaccharide acceptor substrates was determined by monitoring phosphate release in triplicate. The bars indicate means±s.e.m. (C) Mass spectra showing the extension of maltooligosaccharides (DP2 after 22 hours; DP3, DP4 and DP5 after 1 hour) by GlgE in the presence of M1P. (D) Determination of the glycosidic linkage formed by GlgE monitored using $^{1}H$ nuclear magnetic resonance spectroscopy. The upper panel shows a control without enzyme, and the lower panel shows the reaction with enzyme after completion according to the phosphate release assay. (E) Release of M1P from glycogen by Mtb GlgE in the presence of inorganic phosphate analyzed by TLC. (F) ESI-MS analysis of M1P formed in (E) with an expected mass for $[M-H^{+}]^{-}$ of 421.1 Da.
Figure 3C:
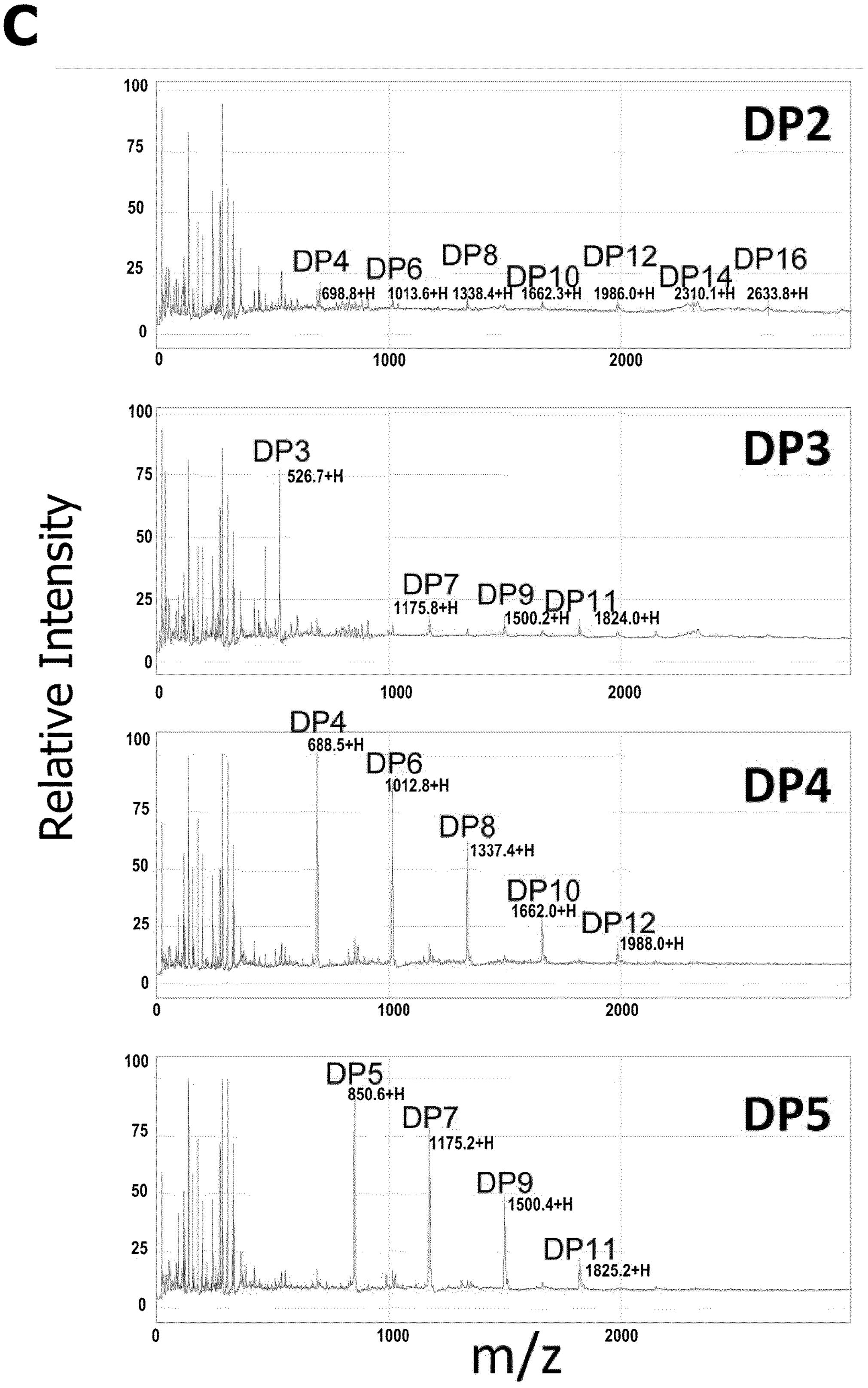
Figures 3D, 3E:
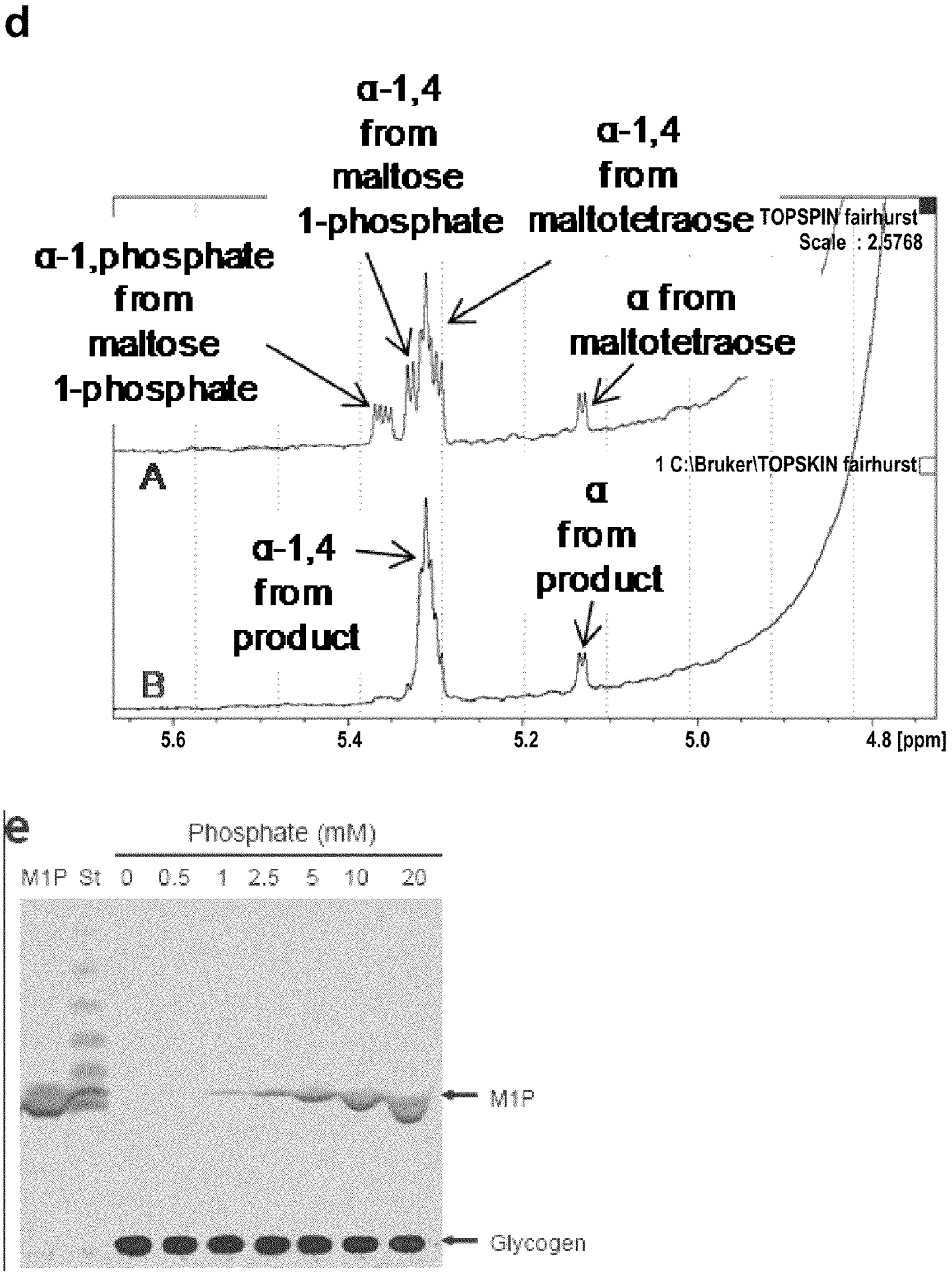

Cytoplasmic M1P accumulation in the *M. smegmatis* ΔglgE mutant suggested that this phosphosugar might be the direct substrate of GlgE. Since the branching enzyme GlgB utilizes linear α-1,4-glucans as a substrate (7), it was hypothesized that GlgE could act as a glycosyl transferase upstream of GlgB, producing these glucose homopolymers by transferring the maltosyl moiety of M1P to the non-reducing end 4-OH of an α-glucan acceptor substrate with concomitant release of the phosphate group (FIG. 3A). In vitro enzymatic activity of His-tagged recombinant GlgE was assayed either quantitatively by monitoring phosphate release from M1P, or qualitatively using mass spectrometry or TLC. Maltooligosaccharides with a degree of polymerization (DP)>4 were efficient acceptors, with DP5 being optimal in the GlgE-catalyzed polymerization of M1P (FIGS. 3B, 3C). The β anomer of M1P at a 1 mM. concentration gave no activity with 1 mM. maltohexaose as the acceptor (detection limit was ≦1% of the activity with the a anomer). The presence of exclusively α-1,4 links in the oligosaccharide products from maltotetraose extension was confirmed by NMR spectroscopy (FIG. 3D). Together, these observations showed that the enzyme exhibits an a retaining mechanism. The activity with maltohexaose was optimal at pH 7.0 and 37° C., consistent with the lifestyle of the organism.

The $K_m^{app}$ for maltohexaose with 5 mM. M1P was 35±8 mM. with a $k_{cat}^{app}$ of 15.4±1.1 $s^{-1}$, revealing a $k_{cat}^{app}/K_m^{app}$ of 440±100 $M^{-1}$ $s^{-1}$, which demonstrates a catalytic efficiency within the typical range for a carbohydrate active enzyme. With 1 mM. M1P, both the $K_m^{app}$ and $k_{cat}^{app}$ of maltohexaose decreased to 13.3±2.4 mM. and to 7.5±0.4 $s^{-1}$, respectively, giving a $k_{cat}^{app}/K_m^{app}$ of 570±110 $M^{-1}$ $s^{-1}$. This trend, coupled with statistically indistinguishable values of $k_{cat}^{app}/K_m^{app}$, is consistent with a substituted-enzyme mechanism, whereby the phosphate- and acceptor-binding sites are synonymous, precluding donor and acceptor molecules binding simultaneously to the enzyme. The $K_m^{app}$ for M1P with 1 mM. maltohexaose was 0.25±0.05 mM. with a $k_{cat}^{app}$ of 1.26±0.07 $s^{-1}$, giving a $k_{cat}^{app}/K_m^{app}$=5,000±1,000 $M^{-1}$ $s^{-1}$, showing that M1P is an efficient donor.

Figure 3F:
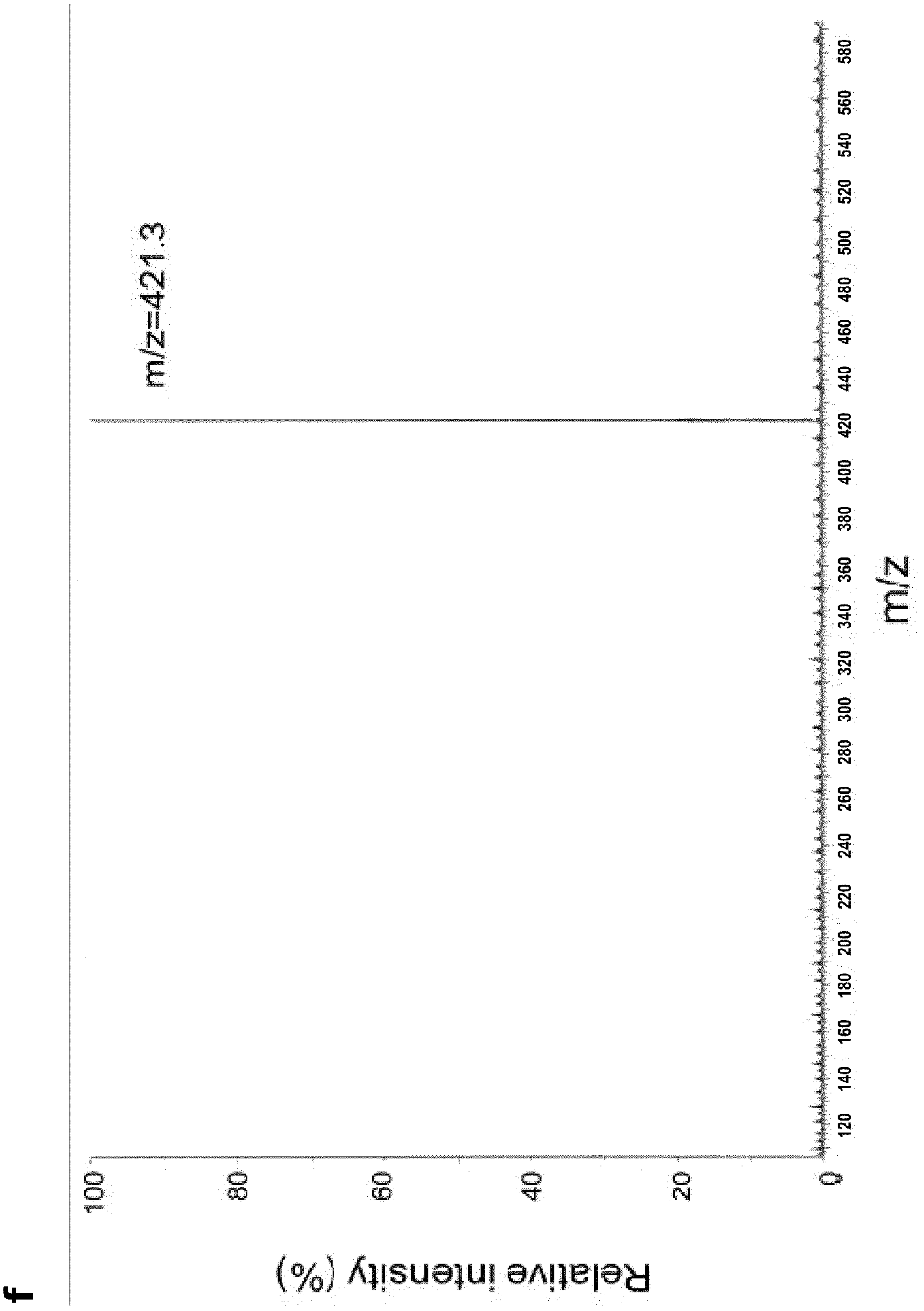

The reversibility of GlgE activity was also tested. Using rabbit liver glycogen as a donor substrate, higher phosphate concentrations resulted in higher M1P production (FIGS. 3E, 3F), confirming the proposed activity of GlgE and its reversibility in vitro. Using the phosphate assay with 125 mM. maltohexaose and 20 mM. inorganic phosphate, ~10% of the phosphate was converted to M1P, showing that the equilibrium is in favor of M1P consumption, as would be expected for this activated sugar. The $K_m^{app}$ for inorganic phosphate was estimated to be 6±4 mM. The enzyme also catalyzed the disproportionation of maltooligosaccharides. Mass spectrometry showed that transfer of maltosyl units from donors with a DP≧4 occurred, but a DP≧6 gave the most rapid transfers. The smallest product of disproportionation had a DP of 4 and the smallest acceptor in this reaction also had a DP of 4, as was the case with M1P as the donor (FIG. 3B).

Figure 4:
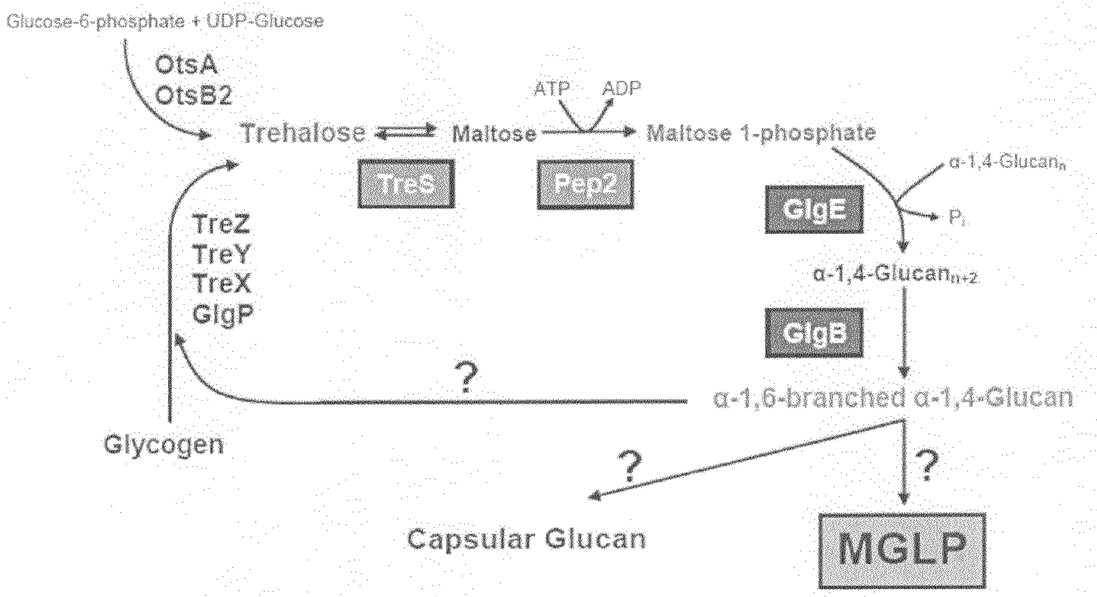
FIG. 4. A novel prokaryotic trehalose-to-α-glucan pathway. The reactions involved in trehalose-to-α-glucan conversion comprise two essential steps in Mtb, catalyzed by GlgE and GlgB.

The unveiling of the M1P-dependent maltosyltransferase activity of GlgE, in combination with the phenotypes of the *M. smegmatis* mutants, allows the plausible conclusion that GlgE is part of a novel pathway in Mtb (and many other phylogenetically distant prokaryotes) that converts trehalose into an α-1,6-branched α-1,4-glucan via four enzymatic steps mediated by TreS, Pep2, GlgE and GlgB (FIG. 4). GlgE not only forms the linear α-1,4-glucan but it can also edit the branch lengths of branched glucan with its disproportionation activity. While three of the four enzymatic activities are well known and have been characterized in Mtb (TreS, GlgB) or related actinomycetes (Pep2), their functional cooperation within a single pathway has eluded precise description due to the lack of awareness of GlgE' s key role.

Mutational Blockage of M1P Formation Suppresses glgE Essentiality in Mtb

Several examples are documented in the literature in which an enzymatic block in sugar catabolic pathways causes accumulation of apparently toxic phosphorylated intermediates that render the mutants sensitive to those sugars. The best known human example is hereditary galactosemia. Patients with this disease cannot metabolize the dietary sugar galactose due to an innate deficiency of the galactose 1-phosphate uridyltransferase GalT, resulting in accumulation of toxic levels of galactose 1-phosphate (12). Similarly, results with the model organism *M. smegmatis* indicates that M1P accumulation is toxic and this might also be the cause of the lethality of glgE mutations in Mtb. To prove the hypothesis of M1P toxicity in Mtb, the frequencies of generating glgE deletion mutations in the WT were compared to those in an isogenic unmarked ΔtreS mutant in Mtb, in which M1P formation is blocked, employing specialized transduction. While unsuccessful in deleting glgE in the WT, the gene could readily be inactivated in the ΔtreS mutant, confirming both the essentiality of GlgE and the causality of M1P toxicity, respectively (FIG. 1C). Likewise, treS inactivation allowed deletion of glgB, demonstrating that M1P toxicity is also the probable cause of GlgB essentiality (FIG. 1D).

Figures 5A, 5B:
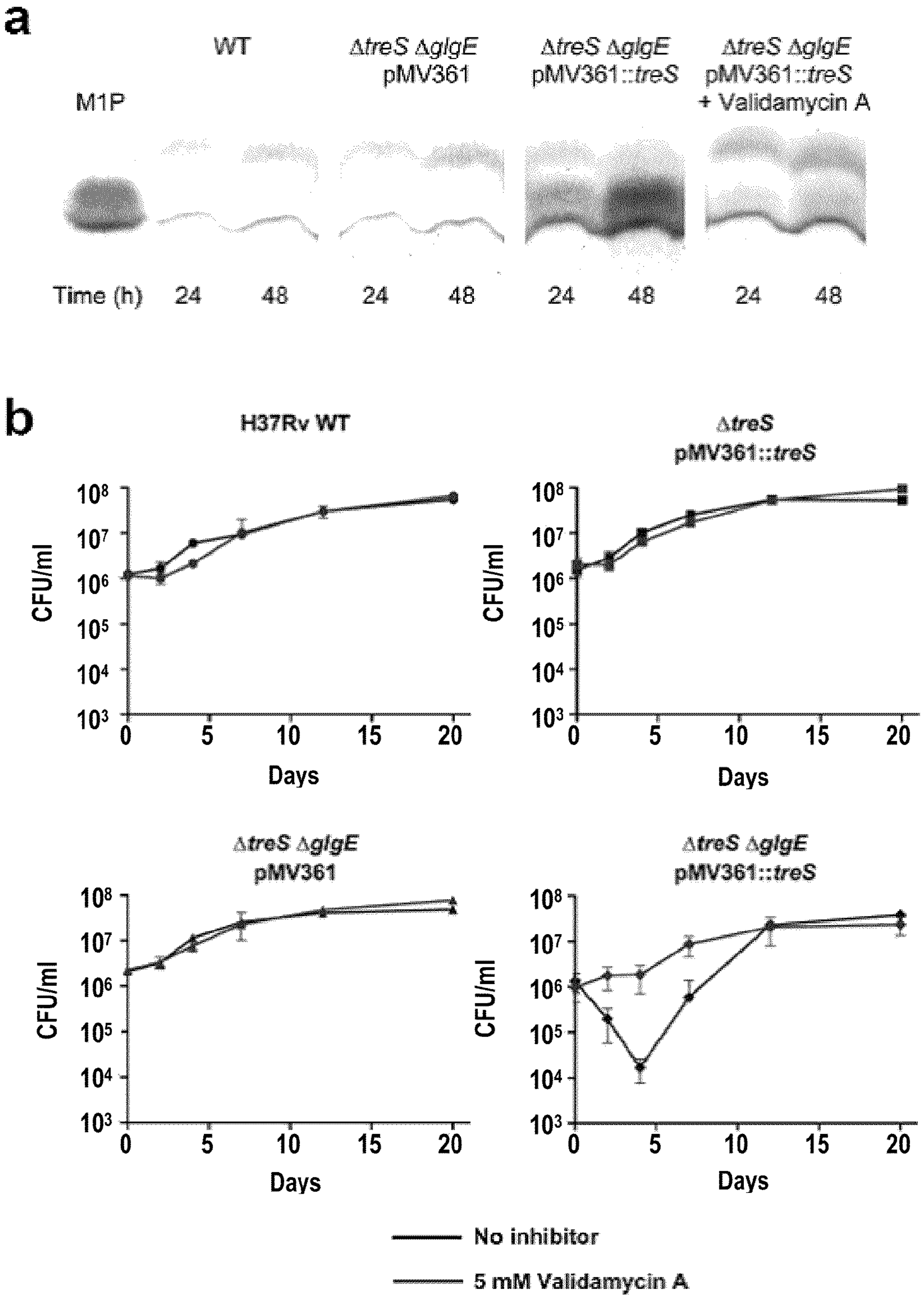
FIG. 5A-5D. M1P self-poisoning is lethal for Mtb grown in vitro and in mice. All strains were precultivated in the presence of 5 mM. VA to log-phase and then subjected to the indicated conditions. (A) GlgE inactivation causes M1P accumulation in a recombinant Mtb H37Rv mutant strain. M1P accumulation was determined by TLC analysis of extracts from cells depleted in VA for 24 or 48 hours. (B) GlgE inactivation is bactericidal in vitro in liquid culture. Viability was determined by quantifying colony forming units (CFU). (C) The conditional lethal mutant strain ΔtreS ΔglgE (pMV361::treS) is killed in a mouse infection model. BALB/c mice were infected intravenously with 106 CFU per animal. (D) TreS is dispensable for virulence in mice. BALB/c mice were infected intravenously with $5\times10^{4}$ CFU per animal. Bacterial burden in organ homogenates in (C) and (D) was determined by counting CFU. The data in (B), (C) and (D) represent means of triplicates±s.d.

GlgE Inactivation in Mtb is Bactericidal In Vitro and in a Mouse Infection Model Next, testing was undertaken to determine whether inactivation of GlgE causes bacteriostasis or lethality in Mtb. Initial attempts to down-regulate the chromosomal expression of glgE with a tetracycline-inducible promoter were unsuccessful, probably because of promoter leakiness resulting in insufficient gene silencing in the absence of the inducer. In an alternative chemical genetic approach, attempts were made to generate a glgE deletion mutant under conditions in which chemical inhibition of TreS was applied in order to prevent M1P toxicity. The inhibitor validamycin A (VA) has been demonstrated to inhibit trehalose synthase TreS from *Bradyrhizobium* species (13). An approach to delete glgE in WT Mtb using specialized transduction in the presence of VA was unsuccessful, probably due to interference with phage infection and/or homologous recombination, since deletion of a non-essential control gene (glgC) under the same conditions also failed. Therefore, it was attempted to mimic the phenotype of a ΔglgE mutant by complementing the ΔtreS ΔglgE double mutant of Mtb with a functional copy of the treS gene provided on an integrative single-copy plasmid in the presence of VA. As expected, treS transformants were obtained in the ΔtreS ΔglgE mutant only in the presence of VA. It was predicted that depletion of the inhibitor would restore TreS enzymatic activity and result in M1P accumulation and cessation of growth in the ΔglgE surrogate strain. M1P was undetectable by TLC in both the WT Mtb and the vector control strain, and accumulated to only low levels in the ΔtreS ΔglgE mutant strain carrying pMV361::treS in the presence of 5 mM VA. In contrast, depletion of the inhibitor resulted in the accumulation of copious amounts of M1P within 48 hours in this ΔglgE surrogate strain (FIG. 5A). Importantly, M1P accumulation correlated with rapid killing of the cells in vitro in liquid culture (2 log reduction in viability within 4 days) (FIG. 5B), demonstrating that GlgE inactivation is lethal in Mtb. Bacteria emerging after the initial killing phase after day 4 did not require supplementation with VA, indicating that they had likely acquired loss-of-function mutations either in the plasmid-encoded treS gene or in the chromosomally located pep2 gene preventing M1P toxicity.

Figures 5C, 5D:
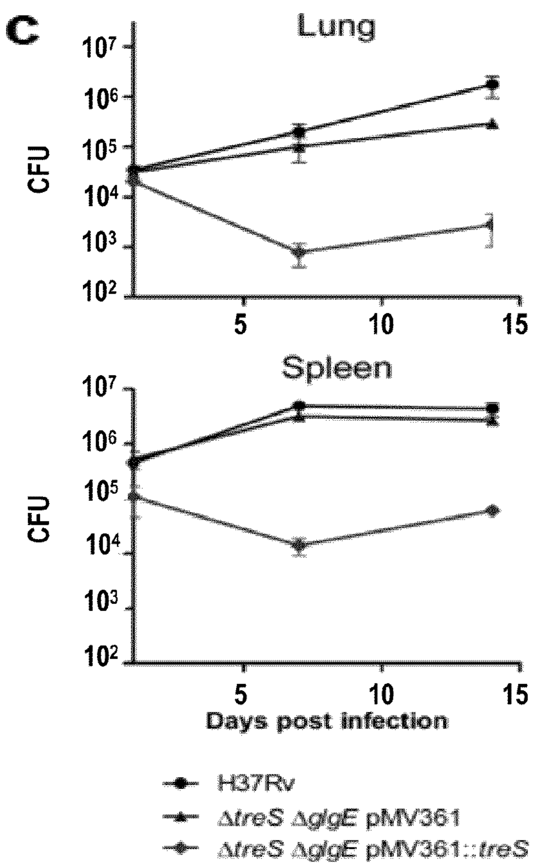

Next, the conditional lethal mutant strain ΔtreS ΔglgE (pMV361::treS) in a mouse infection model was tested (FIG. 5C). This ΔglgE surrogate strain died rapidly in lungs and spleens of infected BALB/c mice (ca. 1.5 log and 1 log reduction of bacterial organ burden within 7 days, respectively). The in vivo killing clearly demonstrates that the TreS-Pep2-GlgE-GlgB pathway (henceforth referred to as the GlgE pathway) is active during growth in the host and that endogenous trehalose levels in Mtb are sufficient to support intracellular M1P accumulation reaching lethal concentrations in vivo. Bacteria surviving the initial killing phase recovered from spleens and lungs at day 14 were all independent of VA. This again suggests a likely acquisition of loss-of-function mutations in either treS or pep2, consistent with the absolute necessity of preventing M1P poisoning in order to allow survival in vivo.

Together, the in vitro and in vivo killing phenotypes convincingly validate GlgE's potential as an attractive drug target candidate. It is noteworthy that the kinetics of killing and of emergence of mutants observed with the ΔglgE surrogate strain in vitro strikingly resemble those reported for treatment of Mtb with a high concentration of the first line drug isoniazid (1 mg/l, equivalent to 20 times the MIC) (14). Remarkably, the GlgE pathway as a whole is dispensable for virulence, as demonstrated by the lack of attenuation of the ΔtreS mutant in mice (FIG. 5D).

A Self-Amplifying Feedback Loop Promotes Overlapping Stress Responses Underlying M1P Lethality In order to gain insight into the molecular mechanisms underlying M1P toxicity and eventual death of Mtb, global gene expression analyses was performed. Interestingly, typical gene expression signatures indicative of unexpected overlapping stress responses in M1P-poisoned Mtb was found. A remodeling of the respiratory electron transport chain was obvious as indicated by significant down-regulation of cytochrome c oxidase (ctaBCDE) as well as up-regulation of components of NADH dehydrogenase I complex (nuoB-DEF), of the non-proton-pumping terminal cytochrome bd oxidase (cydABCD), and of nitrate reductase (narGHIJ). Except for up-regulation of NADH dehydrogenase I, this rearrangement resembles known responses to respiratory inhibitors (15, 16). In fact, in addition to components of the respiratory chain, a striking overall similarity to the transcription profile elicited by the cytochrome c oxidase-specific inhibitor potassium cyanide was observed, clearly suggesting that M1P stress unexpectedly results in inhibition of respiration. A global down-regulation of the dormancy (dosR) regulon was noticed. While the factors triggering induction of this regulon, such as hypoxia, NO, and CO, are well characterized (17, 18), it is unclear which metabolic perturbations stimulate down-regulation. Furthermore, expression of most components of ATP synthase (atpACDEGH) was significantly down-regulated, probably resulting in decreased intracellular ATP levels. This can be linked to the induction of relA triggering the stringent response (19), thus explaining the observed global down-regulation of the translational apparatus. Moreover, M1P stress also led to strong induction of the DNA damage-responsive SOS regulon, including numerous genes involved in DNA repair like recA and the error-prone DNA polymerase dnaE2 (15, 20). Thus, DNA damage appears to be a surprising direct or indirect outcome of M1P self-poisoning.

Most strikingly, another distinct stress response was the up-regulation of a pathway leading to release of trehalose from glycogen, comprising the genes glgP and treXYZ (FIGS. 4, 6C) (21). Apparently, Mtb reacts to M1P stress by increasing the intracellular trehalose level, perhaps as a stress protectant, since trehalose has this function in many bacteria and yeasts (22). However, in the conditional lethal mutant strain ΔtreS ΔglgE (pMV361::treS), this is fatally counterproductive since it promotes further conversion of trehalose to M1P, resulting in a deadly self-amplifying feedback loop that causes progressive self-poisoning.

Synthetic Lethality of the GlgE Pathway with the Glucosyltransferase Rv3032

Figures 6A, 6B:
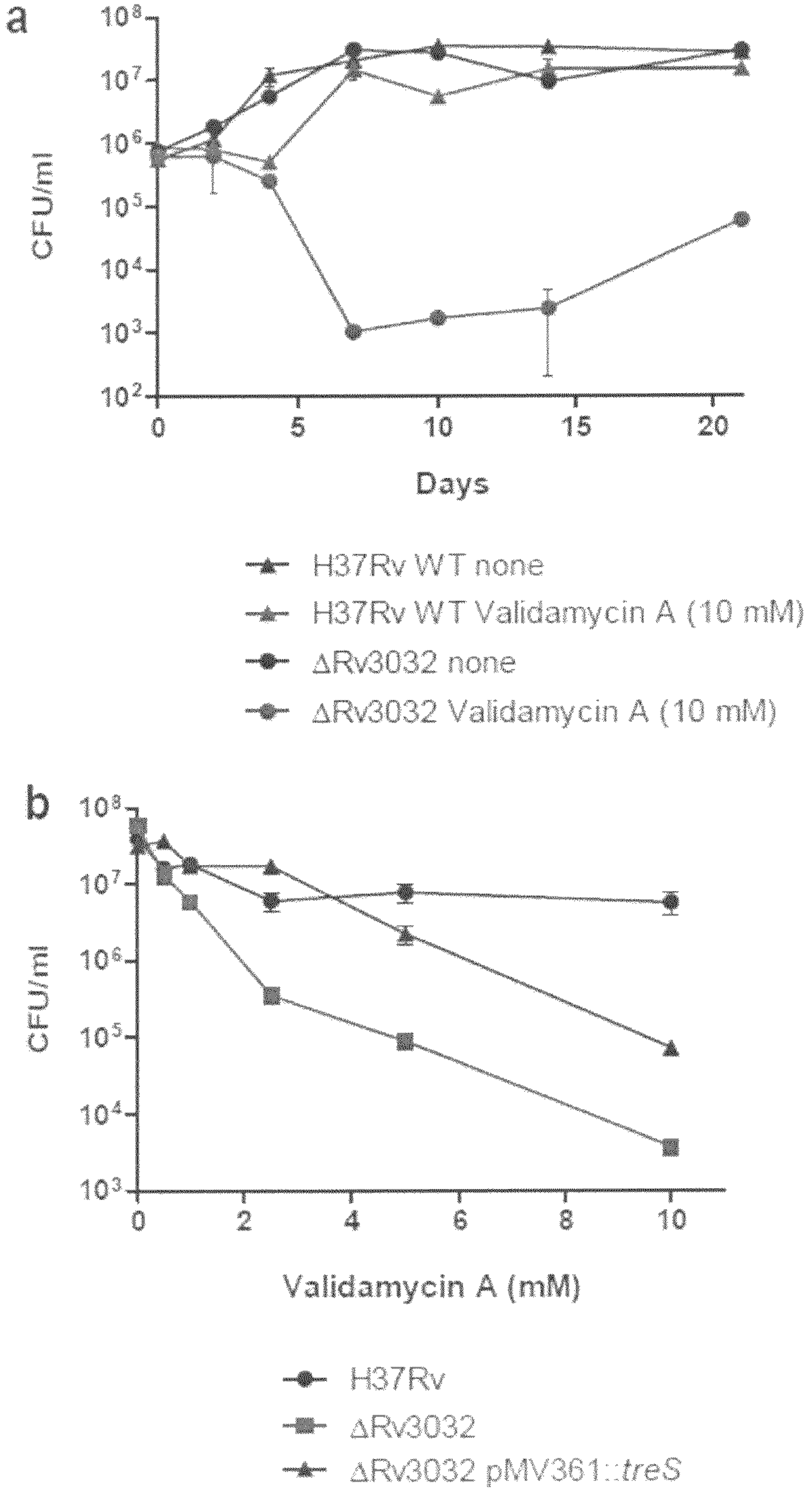
FIG. 6A-6B. Synthetic lethality of treS and Rv3032. (A) Hypersensitivity of the Mtb ΔRv3032 mutant toward the TreS inhibitor VA. (B) Low-level resistance of the Mtb ΔRv3032 mutant against VA mediated by overexpression of the target TreS from an integrative single-copy plasmid. Cultures were inoculated at $5\times10^{6}$ CFU/ml and cultivated for 7 days. The data in (A) and (B) represent means of triplicates±s.e.m. Viability was determined by quantifying CFU.

The novel GlgE pathway is not the only biosynthetic route to α-1,4-glucans in Mtb; two alternative pathways have been described (8). ADP-glucose, formed from glucose 1-phosphate and ATP by ADP-glucose pyrophosphorylase GlgC, is polymerized by glycogen synthase GlgA to linear α-1,4-glucans. Alternatively, the recently described glucosyltransferase Rv3032 can utilize either UDP-glucose or ADP-glucose as the substrate for polymerization to linear α-1,4-glucans (8). When trying to analyze α-1,4-glucan formation in Mtb by combinatorial inactivation of the three known pathways by targeting key steps (GlgC, Rv3032, TreS), it was found that while ΔglgC, ΔtreS, and ΔRv3032 single mutants, as well as ΔglgC ΔtreS and ΔglgC ΔRv3032 double mutants, were all viable, Rv3032 could not be inactivated in the ΔtreS mutant. This suggested the joint essentiality of these two pathways. In order to corroborate this, the sensitivity of the Mtb ΔRv3032 mutant toward the TreS inhibitor VA was tested. While the Mtb WT tolerated high concentrations of the inhibitor (10 mM), the ΔRv3032 mutant was exceptionally sensitive to this compound, causing a 3-log killing over 7 days (FIG. 6A). Furthermore, over-expression of the putative target TreS conferred marked resistance of the ΔRv3032 mutant to VA (FIG. 6B). Together, these data unequivocally validate the joint essentiality (i.e., the synthetic lethality) of treS and Rv3032.

3. Discussion

The rapid emergence of extensively drug-resistant mutants highlights the urgent necessity of finding new classes of drugs to kill Mtb with novel mechanisms of action. The paucity of new TB drugs discovered during the last decades reflects the limited knowledge of essential metabolic processes in Mtb outside the repertoire of known targets such as transcription, translation or mycolic acid biosynthesis. A combination of genetic and biochemical studies has revealed that the M1P-dependent maltosyltransferase GlgE represents such an attractive new class of drug target, which is part of a previously unrecognized α-glucan pathway that has never been targeted by antimicrobials. Studying the function of GlgE has revealed two novel and distinct bactericidal mechanisms to induce death in Mtb. The first death mechanism is suicidal self-poisoning by accumulation of the toxic phosphosugar M1P following GlgE inhibition. This process is driven by a self-amplifying feedback loop that leads to trehalose release from glycogen via the GlgP-TreXYZ pathway, perhaps representing a misled stress protection response that further fuels the accumulation of toxic M1P. The second, and independent, death mechanism is based on the conditional essentiality of GlgE pathway products. Synthetic lethality of the GlgE and Rv3032 pathways indicates that they are involved in the production of related compounds that are reciprocally able to functionally compensate for metabolic or genetic perturbations in the other pathway. This explains why the GlgE pathway as a whole is fully dispensable for the viability and virulence of Mtb as long as the redundant Rv3032 pathway is functioning, but simultaneous inhibition of both pathways is lethal. Rv3032 is involved in the biosynthesis of methylglucose lipopolysaccharides (MGLPs). MGLPs are mycobacteria-specific, methylated and acylated oligomeric α-glucan derivatives that are believed to play an essential regulatory role in fatty acid biosynthesis in Mtb, although their precise physiological function remains speculative (23). Therefore, it is likely that the α-glucan products of the GlgE pathway are subject, at least partially, to further modifications, yielding so far unidentified derivatives structurally and/or functionally related to MGLPs (FIG. 4). Since the two novel bactericidal mechanisms in Mtb are separate and distinct, they will likely work in synergy. This means that, while monotherapy with GlgE inhibitors should be sufficient to kill Mtb as efficiently as treatment with a first line drug such as isoniazid (14), it will likely be possible to dramatically boost the potency of such GlgE inhibitors in a combination therapy with compounds inhibiting the synthetic lethal partner Rv3032. Furthermore, since every step of the GlgE pathway becomes essential when Rv3032 is inactive, combination therapy with Rv3032 inhibitors will also avoid resistance based on loss-of-function mutations in treS or pep2 for evading M1P poisoning. The rapid emergence of such mutants in vitro and in mice indicates that preventing this type of suppressor mechanism could dramatically increase the antitubercular potential of GlgE inhibitors.

This not only has therapeutic, but also general biological significance. The existence of a previously unknown pathway, widespread among prokaryotes, has been established for the conversion of trehalose to α-glucan. Possible connections between the metabolism of these compounds in bacteria have previously been proposed (9, 11, 24). This now convincingly establishes the precise biochemical link through the GlgE pathway. This stems from the discovery that GlgE exhibits a novel (1→4)-α-D-glucan:phosphate α-D-maltosyltransferase activity of the E.C. 2.4.1 hexosyl transferase type. Mtb GlgE is, according to the Carbohydrate Active Enzymes database (http://www.cazy.org) (25) and based on its primary protein sequence, a member of the glycosyl hydrolase subfamily GH13_3, to which no function has yet been ascribed (26). Having defined the catalytic activity of GlgE, for the first time, the function of the other members of this sub-family can be predicted. Although GlgE is a glycosyl hydrolase GH family member and can catalyze transglucosidase reactions (i.e., disproportionation), it is capable of glycosyl transferase reactions with the sugar phosphate donor M1P, a function more typically associated with members of the glycosyl transferase GT family. To date, it appears that GlgE uniquely utilizes a sugar phosphate in a glycosyl transferase reaction for anabolic purposes, while other anabolic glycosyl transferases require sugar nucleoside phosphates or polyprenol phosphates.

The physiological function(s) of the GlgE pathway remains elusive and could be multifaceted (FIG. 4). In addition to MGLP-synthesis and in interaction with the GlgCA and Rv3032 pathways, the GlgE pathway might alternatively participate in α-glucan capsule formation, an extracellular cell wall component potentially important for virulence and persistence of Mtb (8). It could also be involved in the formation of intracellular glycogen, an α-glucan storage polymer from which trehalose can be remobilized via the GlgP-TreXYZ pathway to support trehalose homeostasis (21). Furthermore, since glycogen is a typical intracellular carbon storage compound in many organisms, the GlgE pathway might have a role in Mtb persistence within host microenvironments that exhibit restricted nutrient availability.

It has been shown that the essentiality of GlgE is based on toxicity of its substrate M1P. It has been proposed that the surprising essentiality of GlgB might be due to accumulation of poorly water-soluble linear α-1,4-glucan polymers which are hypothetically toxic (27). However, data presented here demonstrate that the toxicity of M1P, and not that of linear α-1,4-glucans, is the cause that underlies GlgB essentiality, explainable by GlgB's secondary effect on GlgE. In the absence of branching activity, GlgE produces linear α-1,4-glucans that not only have fewer non-reducing ends but also become insoluble once they reach a DP ~20. Therefore, in the absence of GlgB, there will be fewer non-reducing ends available for GlgE to extend, retarding GlgE activity by acceptor substrate limitation that leads to a toxic build up of M1P. Although GlgB could be another potential drug target candidate, the existence of a human orthologue makes it less attractive than GlgE.

M1P accumulation as a result of GlgE inactivation appears to elicit pleiotropic stresses in Mtb, including inhibition of respiration, induction of the stringent response, and DNA damage. Since Mtb can tolerate respiration inhibitors relatively well under aerobic conditions (15, 16) and also maintains viability under conditions such as starvation that trigger the stringent response, DNA damage may be the most critical factor leading to death. At least two alternative, mutually non-exclusive mechanisms could be involved in causing DNA damage. First, reducing monosaccharides and their phosphates can spontaneously form reactive carbonyl species that can non-enzymatically react with DNA in a process called glycation, eventually leading to DNA damage (28). However, since both anomeric carbons are tied up with either the glycoside linkage or bonding of the phosphate group, M1P cannot readily form such carbonyl species without prior cleavage and/or oxidation. Alternatively, DNA damage might occur indirectly through the generation of reactive oxygen species as a result of disturbed respiration. In *E. coli*, up-regulation of NADH dehydrogenase I was found to be a common key response to all tested bactericidal drugs that all lead to hydroxyl radical formation and subsequent induction of the DNA damage-triggered SOS response (29). Intriguingly, up-regulation of components of NADH dehydrogenase I (nuoBDEF) was also observed in M1P-stressed Mtb cultures. This suggests that M1P-induced lethality might share certain aspects of the common mechanism of cellular death caused by bactericidal antibiotics in *E. coli* (29). However, the exact molecular mechanisms underlying M1P toxicity that eventually lead to DNA damage and death is still unknown.

The unique combination of gene essentiality within a synthetic lethal pathway, revealing potential mechanisms not only to boost the potency of inhibitors but also to suppress resistance mutations, distinguishes GlgE from all Mtb drug targets described to date. Self-poisoning by a toxic phosphosugar provoking pleiotropic stresses also implies a novel mechanism to induce death in Mtb that is different from those employed by current TB drugs and reveals α-glucan synthesis, for the first time, as a target for antimicrobials. Thus, there is reason to believe that inhibitors of GlgE, enhanced by Rv3032 inhibitors, could be developed to treat XDR-TB. This exemplifies the great potential for the discovery of new TB drug targets hidden within synthetic lethal pathways.

REFERENCES

1. Dye, C. Global epidemiology of tuberculosis. Lancet 367, 938-940 (2006).
2. Sassetti, C. M., Boyd, D. H. & Rubin, E. J. Genes required for mycobacterial growth defined by high density mutagenesis. Mol Microbiol 48, 77-84 (2003).
3. Sassetti, C. M. & Rubin, E. J. Genetic requirements for mycobacterial survival during infection. Proc Natl Acad Sci USA 100, 12989-12994 (2003).
4. Tong, A. H. et al. Global mapping of the yeast genetic interaction network. Science 303, 808-813 (2004).
5. Boone, C., Bussey, H. & Andrews, B. J. Exploring genetic interactions and networks with yeast. Nat Rev Genet. 8, 437-449 (2007).
6. Belanger, A. E. & Hatfull, G. F. Exponential-phase glycogen recycling is essential for growth of *Mycobacterium smegmatis*. J Bacteriol 181, 6670-6678 (1999).
7. Garg, S. K., Alam, M. S., Kishan, K. V. & Agrawal, P. Expression and characterization of alpha-(1,4)-glucan branching enzyme Rv1326c of *Mycobacterium tuberculosis* H37Rv. Protein Expr Purif 51, 198-208 (2007).
8. Sambou, T. et al. Capsular glucan and intracellular glycogen of *Mycobacterium tuberculosis*: biosynthesis and impact on the persistence in mice. Mol Microbiol 70, 762-774 (2008).
9. Pan, Y. T. et al. Trehalose synthase converts glycogen to trehalose. FEBS J 275, 3408-3420 (2008).
10. Pan, Y. T. et al. Trehalose synthase of *Mycobacterium smegmatis*: purification, cloning, expression, and properties of the enzyme. Eur J Biochem 271, 4259-4269 (2004).
11. Jarling, M., Cauvet, T., Grundmeier, M., Kuhnert, K. & Pape, H. Isolation of mak1 from *Actinoplanes missouriensis* and evidence that Pep2 from *Streptomyces coelicolor* is a maltokinase. J Basic Microbiol 44, 360-373 (2004).
12. Bosch, A. M. Classical galactosaemia revisited. J Inherit Metab Dis 29, 516-525 (2006).
13. Streeter, J. G. & Gomez, M. L. Three enzymes for trehalose synthesis in *Bradyrhizobium* cultured bacteria and in bacteroids from soybean nodules. Appl Environ Microbiol 72, 4250-4255 (2006).
14. Karakousis, P. C., Williams, E. P. & Bishai, W. R. Altered expression of isoniazid-regulated genes in drug-treated dormant *Mycobacterium tuberculosis*. J Antimicrob Chemother 61, 323-331 (2008).
15. Boshoff, H. I. et al. The transcriptional responses of *Mycobacterium tuberculosis* to inhibitors of metabolism: novel insights into drug mechanisms of action. J Biol Chem 279, 40174-40184 (2004).
16. Manjunatha, U., Boshoff, H. I. & Barry, C. E. The mechanism of action of PA-824: Novel insights from transcriptional profiling. Commun Integr Biol 2, 215-218 (2009).
17. Kumar, A. et al. Heme oxygenase-1-derived carbon monoxide induces the *Mycobacterium tuberculosis* dormancy regulon. J Biol Chem 283, 18032-18039 (2008).
18. Voskuil, M. I. et al. Inhibition of respiration by nitric oxide induces a *Mycobacterium tuberculosis* dormancy program. J Exp Med 198, 705-713 (2003).
19. Dahl, J. L. et al. The role of RelMtb-mediated adaptation to stationary phase in long-term persistence of *Mycobacterium tuberculosis* in mice. Proc Natl Acad Sci USA 100, 10026-10031 (2003).
20. Boshoff, H. I., Reed, M. B., Barry, C. E., 3rd & Mizrahi, V. DnaE2 polymerase contributes to in vivo survival and the emergence of drug resistance in *Mycobacterium tuberculosis*. Cell 113, 183-193 (2003).
21. Murphy, H. N. et al. The OtsAB pathway is essential for trehalose biosynthesis in *Mycobacterium tuberculosis*. J Biol Chem 280, 14524-14529 (2005).
22. Arguelles, J. C. Physiological roles of trehalose in bacteria and yeasts: a comparative analysis. Arch Microbiol 174, 217-224 (2000).
23. Jackson, M. & Brennan, P. J. Polymethylated polysaccharides from *Mycobacterium* species revisited. J Biol Chem 284, 1949-1953 (2009).
24. Schneider, D., Bruton, C. J. & Chater, K. F. Duplicated gene clusters suggest an interplay of glycogen and trehalose metabolism during sequential stages of aerial mycelium development in *Streptomyces coelicolor* A3(2). Mol Gen Genet. 263, 543-553 (2000).
25. Cantarel, B. L. et al. The Carbohydrate-Active EnZymes database (CAZy): an expert resource for Glycogenomics. Nucleic Acids Res 37, D233-238 (2009).
26. Stam, M. R., Danchin, E. G. J., Rancurel, C., Coutinho, P. M. & Henrissat, B. Dividing the large glycoside hydrolase family 13 into subfamilies: towards improved functional annotations of α-amylase-related proteins. Protein Eng. Des. Sel. 19, 555-562 (2006).
27. Kaur, D., Guerin, M. E., Skovierova, H., Brennan, P. J. & Jackson, M. Chapter 2 Biogenesis of the cell wall and other glycoconjugates of *Mycobacterium tuberculosis*. Adv Appl Microbiol 69, 23-78 (2009).
28. Barea, F. & Bonatto, D. Relationships among carbohydrate intermediate metabolites and DNA damage and repair in yeast from a systems biology perspective. Mutat Res 642, 43-56 (2008).
29. Kohanski, M. A., Dwyer, D. J., Hayete, B., Lawrence, C. A. & Collins, J. J. A common mechanism of cellular death induced by bactericidal antibiotics. Cell 130, 797-810 (2007).

30. Bardarov, S. et al. Specialized transduction: an efficient method for generating marked and unmarked targeted gene disruptions in *Mycobacterium tuberculosis, M. bovis* BCG and *M. smegmatis*. Microbiology 148, 3007-3017 (2002).

31. Lanzetta, P. A., Alvarez, L. J., Remack, P. S. & Candia, 0. A. An improved assay for nanomole amounts of inorganic phosphate. Anal. Biochem. 100, 95-97 (1979).

32. Saeed, A. I. et al. TM4: a free, open-source system for microarray data management and analysis. Biotechniques 34, 374-378 (2003).

33. Bardarov, S. et al. Specialized transduction: an efficient method for generating marked and unmarked targeted gene disruptions in *Mycobacterium tuberculosis, M. bovis* BCG and *M. smegmatis*. Microbiology 148, 3007-3017 (2002).

34. Stover, C. K. et al. New use of BCG for recombinant vaccines. Nature 351, 456-460 (1991).

35. Besra, G. S. et al. A new interpretation of the structure of the mycolyl-arabinogalactan complex of *Mycobacterium tuberculosis* as revealed through characterization of oligoglycosylalditol fragments by fast-atom bombardment mass spectrometry and 1H nuclear magnetic resonance spectroscopy. Biochemistry 34, 4257-4266 (1995).

What is claimed is:

1. A method for determining whether an agent is a putative antibacterial, the method comprising experimentally determining whether or not the agent inhibits the maltosyltransferase GlgE (GlgE) by measuring GlgE activity in the presence of the agent;

wherein determining whether the agent inhibits GlgE comprises contacting GlgE with the agent in the presence of maltose-1-phosphate and maltooligosaccharide and measuring GlgE activity;

wherein an agent that reduces GlgE activity is determined to inhibit GlgE and is identified as a putative antibacterial.

2. The method of claim 1, wherein measuring GlgE activity comprises measuring the release of inorganic phosphate.

3. The method of claim 1, wherein measuring GlgE activity comprises measuring maltooligosaccharide elongation or maltose 1-phosphate consumption.

4. The method of claim 1, wherein measuring GlgE activity comprises measuring disproportionation activity.

5. The method of claim 1, wherein determining whether the agent inhibits GlgE activity comprises contacting bacterial cells comprising GlgE with the agent and measuring GlgE activity.

6. The method of claim 1, further comprising contacting bacterial cells with agent that inhibits GigE activity and measuring bacterial cell viability.

7. The method of claim 1, wherein the agent is selected from the group consisting of: a chemical, small molecule, polypeptide, saccharide, protein, protein fragment, or aptamer.

8. The method of claim 1, wherein the antibacterial is effective against mycobacteria.

9. The method of claim 1, wherein the antibacterial is effective against an opportunistic pathogen.

10. The method of claim 6, wherein the bacterial cells are in presence of trehalose.

11. The method of claim 6, the method additionally comprising one or more controls comprising:

measuring bacterial cell viability in the absence of the agent; and/or contacting bacterial cells with the agent in the absence of trehalose and measuring bacterial cell viability; and/or contacting bacterial cells with inoperable trehalose synthase (TreS), or pea pathogenicity (Pep2) protein with the agent; and measuring bacterial cell viability.

12. The method of claim 6, wherein cell viability is measured after between 24 and 192 hours.

13. The method of claim 8, wherein the mycobacteria are selected from the group consisting of *Mycobacterium tuberculosis, Mycobacterium bovis, Mycobacterium bovis* BCG, *Mycobacterium smegmatis* and δglgE *Mycobacterium smegmatis.*

14. The method of claim 9, wherein the opportunistic pathogen is from genus *Pseudomonas*, or genus *Burkholderia.*

* * * * *